US010482748B2

(12) United States Patent
Struhsaker et al.

(10) Patent No.: US 10,482,748 B2
(45) Date of Patent: Nov. 19, 2019

(54) METHOD AND SYSTEM FOR MONITORING LIVESTOCK

(71) Applicant: TIONESTA, LLC, Austin, TX (US)

(72) Inventors: Paul Struhsaker, Austin, TX (US); Paul Posner, Austin, TX (US); Michael Landers, Austin, TX (US); Nicholas Armstrong, Austin, TX (US)

(73) Assignee: TIONESTA, LLC, Austin, TX (US)

( * ) Notice: Subject to any disclaimer, the term of this patent is extended or adjusted under 35 U.S.C. 154(b) by 0 days.

(21) Appl. No.: 16/163,080

(22) Filed: Oct. 17, 2018

(65) Prior Publication Data

US 2019/0130728 A1 May 2, 2019

Related U.S. Application Data

(63) Continuation of application No. 15/799,302, filed on Oct. 31, 2017.

(51) Int. Cl.
*H04W 4/02* (2018.01)
*G08B 21/18* (2006.01)
(Continued)

(52) U.S. Cl.
CPC ............ *G08B 21/18* (2013.01); *A01K 11/008* (2013.01); *A01K 29/005* (2013.01); *A61B 5/00* (2013.01); *G01S 5/0263* (2013.01); *H04L 67/025* (2013.01); *H04L 67/125* (2013.01); *H04W 4/021* (2013.01); *H04W 4/029* (2018.02); *H04W 4/38* (2018.02); *H04W 4/70* (2018.02); *H04W 4/80* (2018.02); *H04W 88/10* (2013.01);
(Continued)

(58) Field of Classification Search
None
See application file for complete search history.

(56) References Cited

U.S. PATENT DOCUMENTS

| 9,848,577 | B1 * | 12/2017 | Brandao | ............... | A01K 11/004 |
| 2005/0145187 | A1 * | 7/2005 | Gray | .................... | A01K 11/008 |
| | | | | | 119/174 |

(Continued)

OTHER PUBLICATIONS

International Search Report and Written Opinion in corresponding International Application No. PCT/US2018/057994, dated Mar. 29, 2019 (37 pages).

*Primary Examiner* — Brent Swarthout
(74) *Attorney, Agent, or Firm* — Osha Liang LLP

(57) ABSTRACT

A system for monitoring livestock in a ranching environment. The system includes tag sensors attached to animals, and configured to collect monitoring data from the animals, a first access point, configured to receive the collected monitoring data from the tag sensors and to process the collected monitoring data, an Internet of Things (IoT) link established between each of the tag sensors and the access point, and an IoT communication protocol overlay that enables synchronized uplinks from the tag sensors to the first access point via the IoT links. The IoT communication protocol overlay governs transmissions of monitoring data by the tag sensors to the access point. The system further includes a hub/cloud platform configured to receive the processed monitoring data from the first access point, perform data analytics on the processed monitoring data, and provide a user interface that enables a user to monitor the livestock.

14 Claims, 18 Drawing Sheets

(51) Int. Cl.

| | | |
|---|---|---|
| *G01S 5/02* | (2010.01) | |
| *A01K 29/00* | (2006.01) | |
| *A01K 11/00* | (2006.01) | |
| *H04L 29/08* | (2006.01) | |
| *A61B 5/00* | (2006.01) | |
| *H04W 4/021* | (2018.01) | |
| *H04W 88/10* | (2009.01) | |
| *H04W 4/38* | (2018.01) | |
| *H04W 4/029* | (2018.01) | |
| *H04W 4/70* | (2018.01) | |
| *H04W 4/80* | (2018.01) | |
| *G01S 19/13* | (2010.01) | |
| *H04B 5/00* | (2006.01) | |
| *H04W 84/12* | (2009.01) | |
| *H04W 92/20* | (2009.01) | |
| *H04B 17/318* | (2015.01) | |
| *A61B 5/01* | (2006.01) | |
| *A61B 5/021* | (2006.01) | |
| *A61B 5/024* | (2006.01) | |
| *A61B 5/11* | (2006.01) | |
| *H04W 84/18* | (2009.01) | |

(52) U.S. Cl.
CPC .................. *A61B 5/01* (2013.01); *A61B 5/021* (2013.01); *A61B 5/024* (2013.01); *A61B 5/1112* (2013.01); *A61B 5/1123* (2013.01); *A61B 5/6861* (2013.01); *A61B 2503/40* (2013.01); *G01S 19/13* (2013.01); *H04B 5/0062* (2013.01); *H04B 17/318* (2015.01); *H04L 67/10* (2013.01); *H04L 67/12* (2013.01); *H04W 84/12* (2013.01); *H04W 84/18* (2013.01); *H04W 92/20* (2013.01)

(56) References Cited

U.S. PATENT DOCUMENTS

| | | |
|---|---|---|
| 2009/0063187 A1 | 3/2009 | Johnson et al. |
| 2014/0064181 A1* | 3/2014 | Srivastava ............ H04W 84/18 370/328 |
| 2014/0274139 A1 | 9/2014 | Bilal et al. |
| 2016/0037755 A1* | 2/2016 | Webster .............. G06F 19/3418 600/304 |
| 2017/0367305 A1* | 12/2017 | Castro Lisboa ....... A61D 17/00 |
| 2017/0373790 A1* | 12/2017 | Curtis .................. H04L 1/0006 |

* cited by examiner

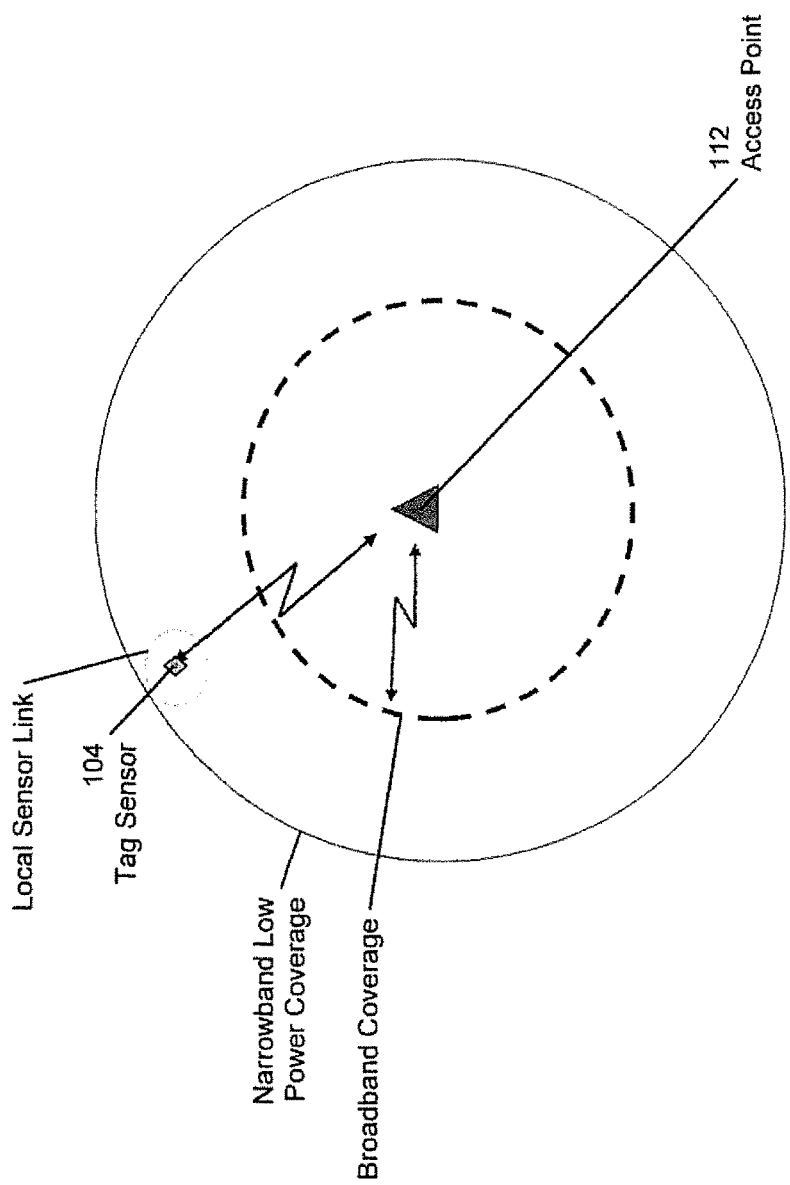

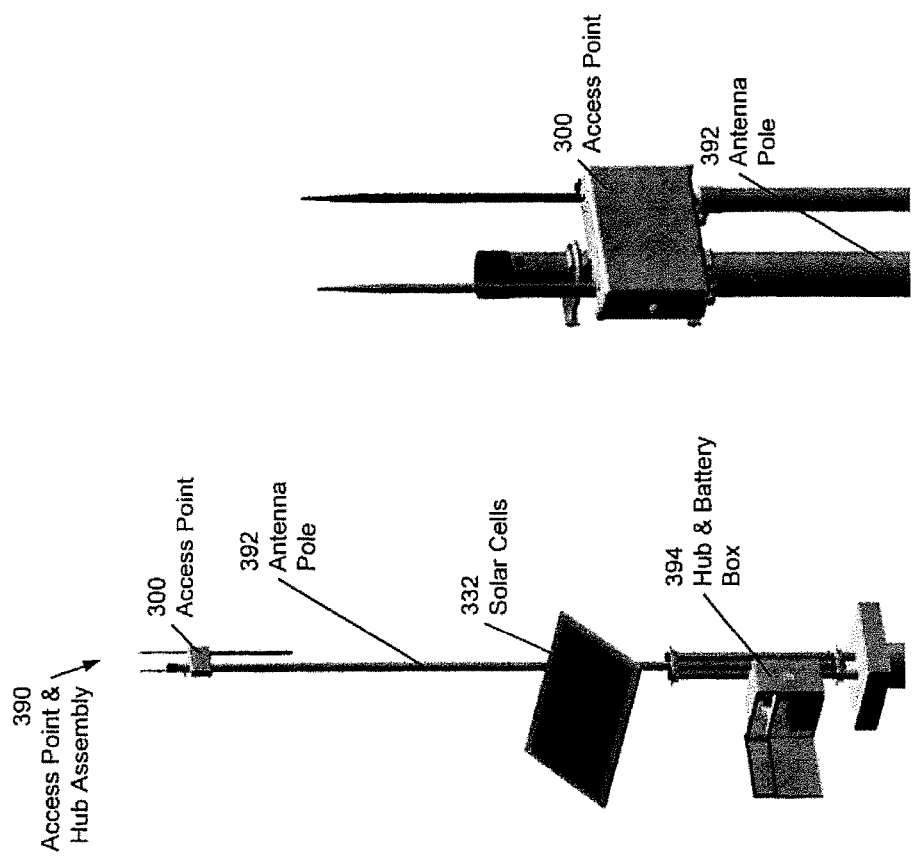
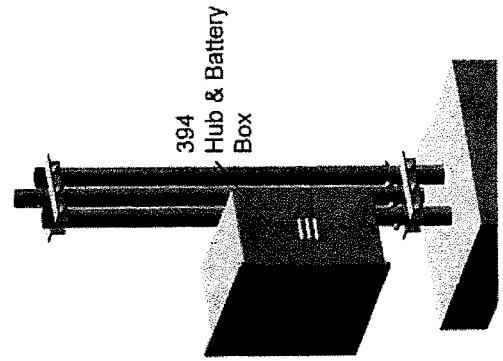
FIG. 3E
FIG. 3D
FIG. 3C

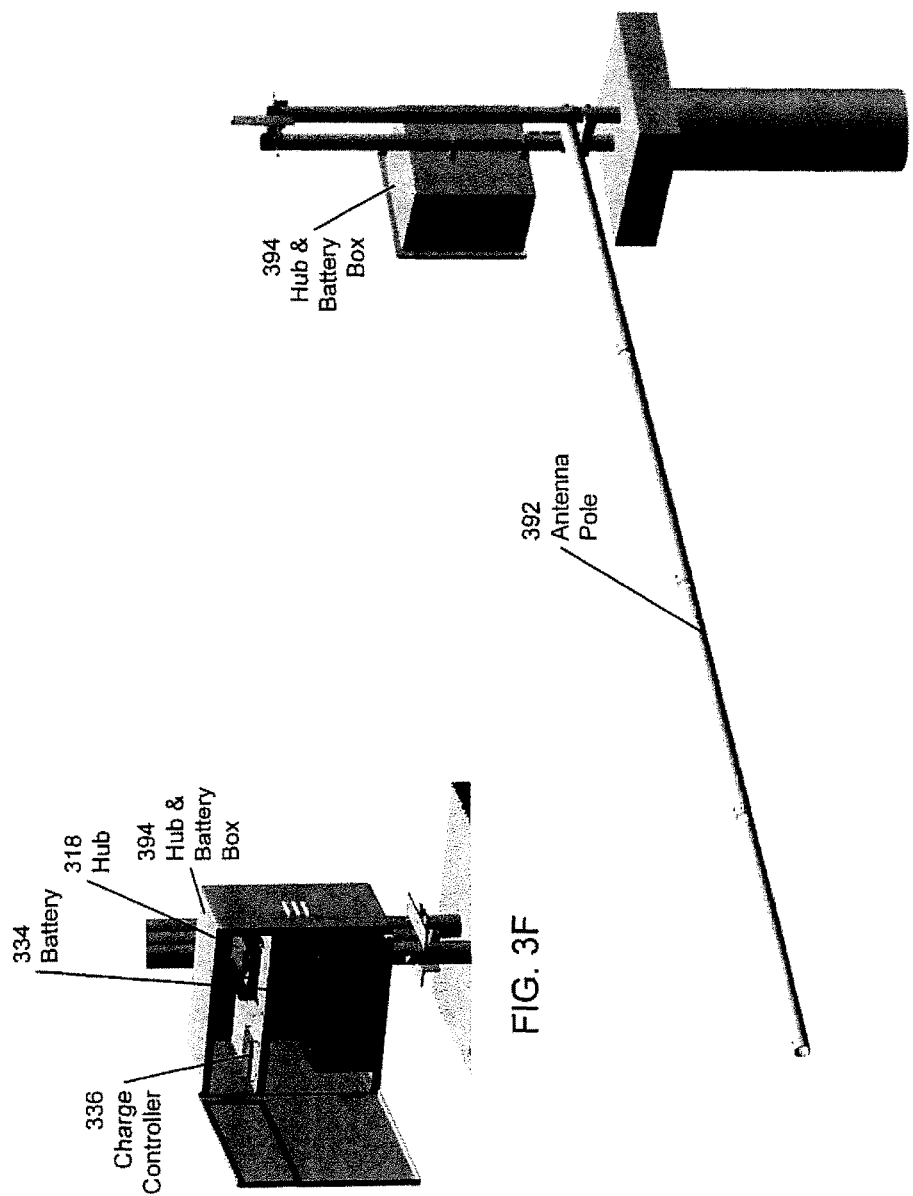

METHOD AND SYSTEM FOR MONITORING LIVESTOCK

This application is a Continuation of application Ser. No. 15/799,302 filed Oct. 31, 2017, and now U.S. Pat. No. 10,242,547.

BACKGROUND

Ranching of cattle, sheep, goats or any other animals raised for commercial use may require the monitoring of these animals as they move across potentially large areas to ensure their safety and well-being. This may include, for example, monitoring the location of the animals, their behavior and/or physiological variables.

SUMMARY

In general, in one aspect, the invention relates to a system for monitoring livestock in a ranching environment. The system comprises: tag sensors attached to animals, and configured to collect monitoring data from the animals; a first access point, configured to receive the collected monitoring data from the tag sensors and to process the collected monitoring data; an Internet of Things (IoT) link established between each of the tag sensors and the access point; an IoT communication protocol overlay that enables synchronized uplinks from the tag sensors to the first access point via the IoT links, wherein the IoT communication protocol overlay governs transmissions of monitoring data by the tag sensors to the access point; and a hub/cloud platform configured to: receive the processed monitoring data from the first access point; perform data analytics on the processed monitoring data; and provide a user interface that enables a user to monitor the livestock.

In general, in one aspect, the invention relates to a system for monitoring livestock in a ranching environment. The system comprises: a two-tier access point comprising a first tier broadband communication interface and a second tier narrowband communication interface, and configured to: receive, using the narrowband interface, monitoring data from tag sensors that are attached to animals and configured to collect the monitoring data from the animals; and transmit, using the broadband interface, the received monitoring data to a hub/cloud platform that provides a user interface enabling a user to monitor the livestock.

BRIEF DESCRIPTION OF DRAWINGS

FIGS. 1A-1H show systems for monitoring livestock, in accordance with one or more embodiments of the invention.

FIGS. 3A-3G show access points of a system for monitoring livestock, in accordance with one or more embodiments of the invention.

DETAILED DESCRIPTION

Figure 1A:
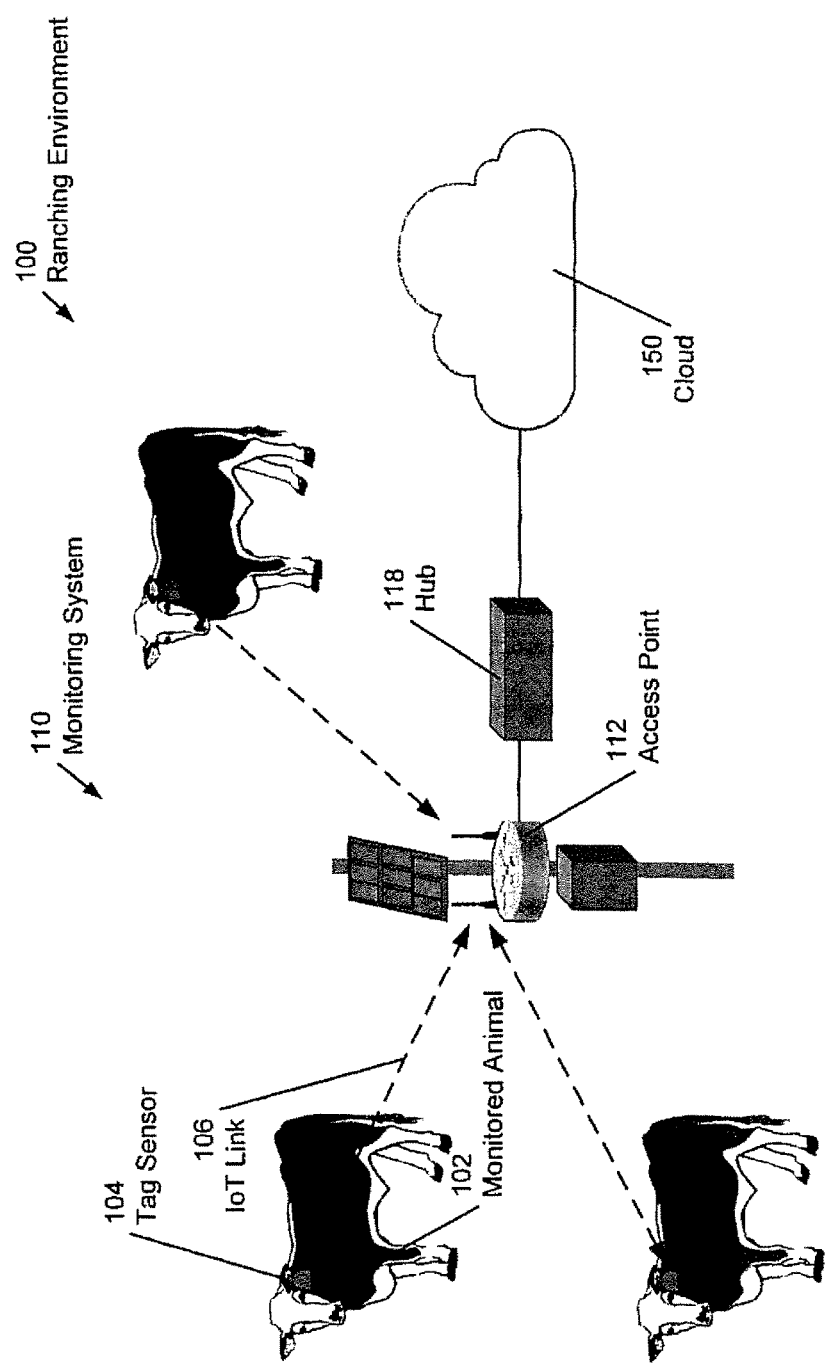

Specific embodiments of the invention will now be described in detail with reference to the accompanying figures. Like elements in the various figures are denoted by like reference numerals for consistency. Like elements may not be labeled in all figures for the sake of simplicity.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1A-8, any component described with regard to a figure, in various embodiments of the invention, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments of the invention, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that, one or more of the steps shown in the flowcharts may be omitted, repeated, and/or performed in a different order than the order shown. Accordingly, the scope of the invention should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

In general, embodiments of the invention are directed to methods and systems for monitoring livestock. Ranching of cattle, sheep, goats or any other animals raised for commercial use may require the monitoring of these animals as they move across potentially large areas to ensure their safety and well-being. Embodiments of the invention enable the monitoring of these commercially valuable animals over large areas of tens of thousands of acres, using sensors, as subsequently described.

FIGS. 1A-1D show systems for monitoring livestock, in accordance with one or more embodiments of the invention. Turning to FIG. 1A, a ranching environment (100), in accordance with one or more embodiments of the invention, is shown. The ranching environment (100) may include farmland used to raise cattle, sheep, goats, or any other type of animal. The animals are monitored by the system for monitoring livestock (110). More specifically, each monitored animal (102) is equipped with a tag sensor (104) that communicates with an access point (112) to enable monitoring of the animals. The access point (112), in one or more embodiments of the invention, is configured to communicate with the tag sensors (104) of the monitored animals (102) via an Internet of Things (IoT) link (106). The access point may further interface with a hub (118), which may perform processing of the data received from the monitored animals via the access points, as further described below. In one or more embodiments of the invention, data gathered from the animals is uploaded to a cloud environment (150), from where they may be accessible to users. Additionally or alternatively, the data may also be locally accessible via the hub or via the access point, as further described below. Each of the components of the system for monitoring livestock is subsequently described in detail, with reference to FIGS. 2A-7.

Figure 1B:
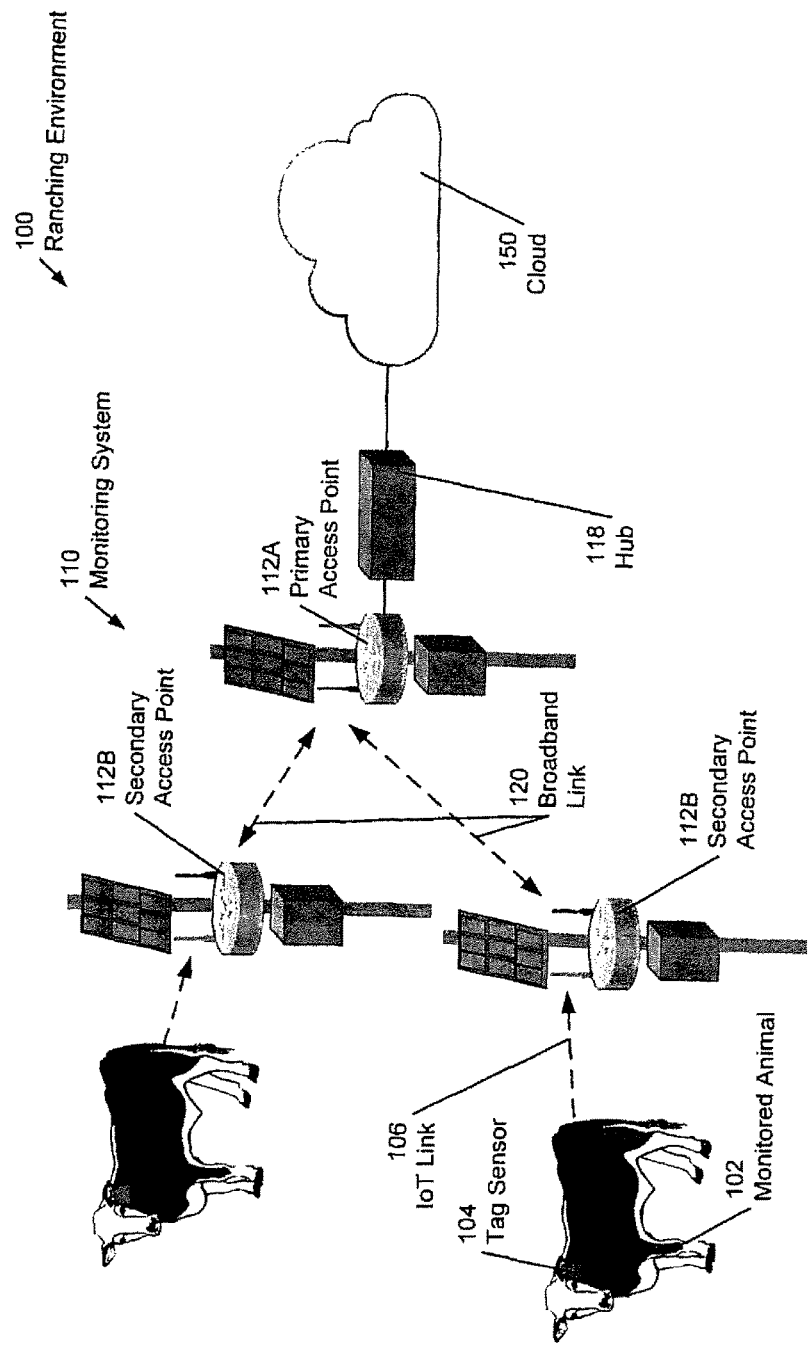

Turning to FIG. 1B, an alternative configuration of a system for monitoring livestock (110), in accordance with one or more embodiments of the invention, is shown. Unlike the system shown in FIG. 1A, the system of FIG. 1B includes multiple access points (112A, 112B). Each access point may have a limited range that may depend on the transmission power of the access point, but also on the transmission power of the tag sensors (104) of the monitored animals (102). Accordingly, in order to cover larger environments (100) with monitoring services, multiple access points may be placed at different locations in the environment. FIG. 1B shows a primary access point (112A) and two secondary access points (112B). While the primary access point (112A) may directly interface with the hub (118), e.g., using a wired broadband link such as an Ethernet interface, the secondary access points may interface with the primary access point (112A) using a broadband link (120) such as a wireless local area network (WLAN) based on, e.g., the Wi-Fi standard. Using additional access points, distributed across the ranching environment (100), larger areas may thus be covered by the system for monitoring livestock (110). Those skilled in the art will appreciate that various configurations of multiple access points are feasible without departing from the invention. For example, systems for monitoring livestock may include any number of access points to monitor environments of any size. Further, multiple access points may directly interface with the hub (similar to the primary access point (112A)). Alternatively or additionally, multiple access points may increase the monitored area using a daisy chain configuration (i.e., tertiary access points may interface with the secondary access points, analogous to how the secondary access points interface with the primary access point). Further, in hybrid configurations, some access points may be daisy-chained, whereas other access points may directly interface with the hub. In one embodiment of the invention, an access point or multiple access points may be directly connected to the cloud, e.g., when a reliable connection to the cloud is continuously available.

Figure 1C:
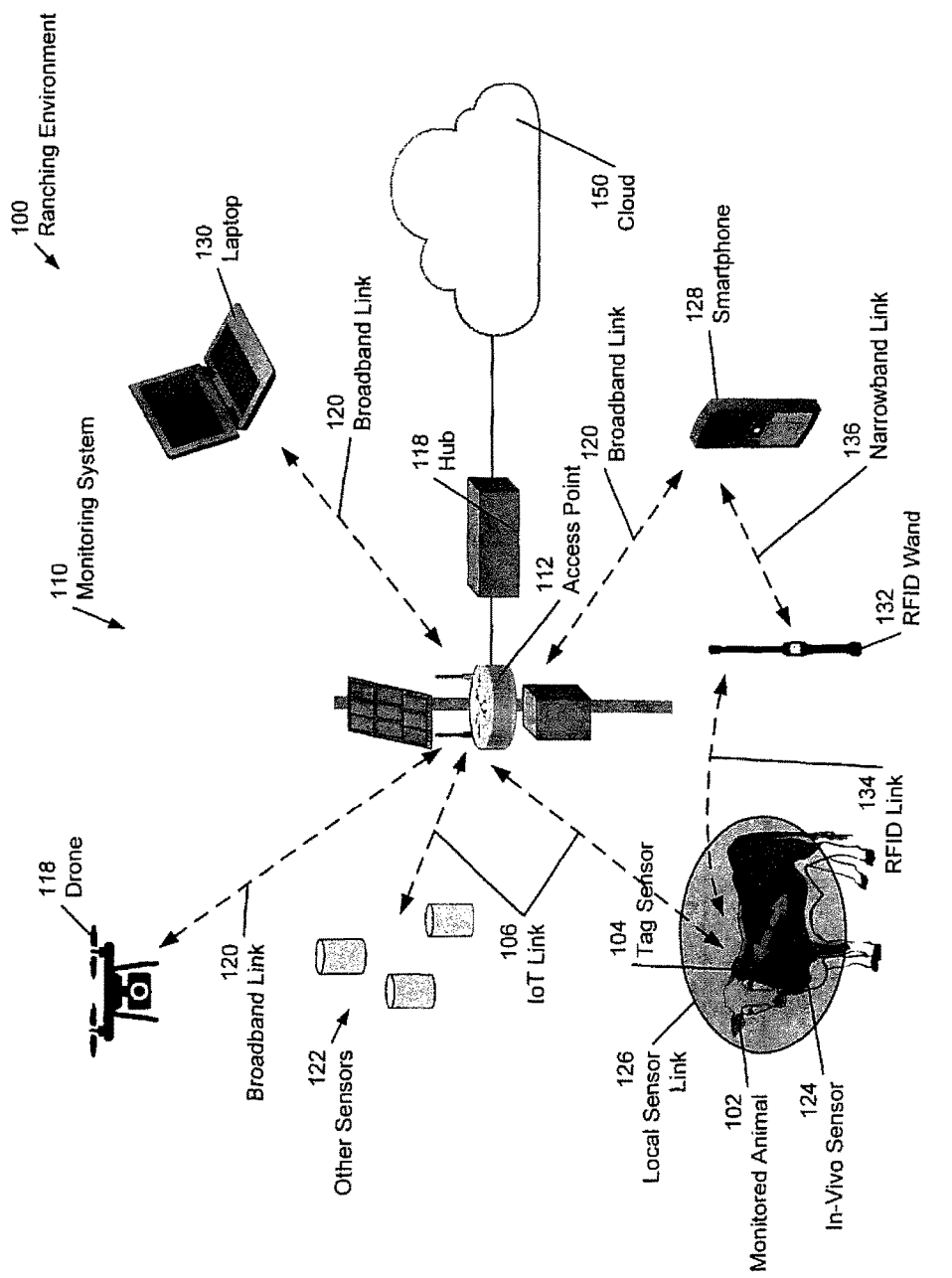

Turning to FIG. 1C, another alternative configuration of a system for monitoring livestock, in accordance with one or more embodiments of the invention, is shown. The system includes additional components that may facilitate the use of the monitoring system and/or provide additional features. In one embodiment of the invention, the broadband link (120) of the access point (112) is used to provide user access to the monitoring system (110). More specifically, user devices such as smartphones (128) or laptops (130) may connect to the access point (112) via the broadband link (120) in order to obtain monitoring data, to configure the monitoring system, etc. Data that are provided by the tag sensors (104) and/or tag sensor data that have been collected, processed and/or stored by the hub (118) may be obtained via a hub/cloud platform, described in FIGS. 2A and 2B.

In one or more embodiments of the invention, the broadband link may further be used to interface additional devices with access points (112) of the monitoring system (110). In FIG. 1C, a drone (118) is shown, communicating with the access point (112) via the broadband link (120). The drone may further enhance the monitoring capabilities of the monitoring system (110). The drone may, for example, be equipped with a camera and/or other sensors and may be in contact with various access points, depending on the drone's current location in the ranching environment (100). The drone may further not necessarily be in continuous contact with an access point and may, instead, operate autonomously and may only require periodic contact with an access point. One or more drones (118) may be used to visually inspect a ranch. Multispectral cameras and/or mosaic photography may be used to monitor moisture, pasture, crop growth, etc. using additional analytics software.

Other sensors that rely on a broadband link (160) via one of the access points (112), may be part of the monitoring system as well. For example, cameras that are equipped with a Wi-Fi interface may be used to visually monitor certain areas of the ranching environment (100). Such cameras may include motion detection to detect people and/or predators. Additionally or alternatively, cameras may provide still photos, video clips or live videos and/or alarms based on a detection of certain events in the videos or photos. In addition, the broadband link (160) may be used for any other purposes such as voice over IP and/or for any other high data rate service.

In one or more embodiments of the invention, the monitoring system (110), using the IoT link (106), not only monitors the tag sensors (104), but also other sensors (122). The other sensors may perform environmental measurements such as air temperature, humidity, or may be used to monitor equipment such as gates, feeders, water sources, propane tanks, etc.

One or more embodiments of the invention further support in-vivo sensing using an in-vivo sensor (124). The in-vivo sensor may be an implanted capsule, e.g., a capsule inserted under the skin of the animal, an ingested capsule, a skin or surface patch, a clip or any other type of sensor that provides monitoring functionalities that extend the capabilities of the tag sensor (104). The in-vivo sensing may include obtaining one or more physiological measurements of the animal. A local sensor link (126) may transmit the measurements obtained by the in-vivo sensor (124) to the tag sensor (104), which may relay these measurements to one of the access points (112). An exemplary in-vivo sensing capsule is further discussed below, with reference to FIGS. 5A and 5B.

In one or more embodiments of the invention, the access point (112) is a two-tier access point equipped with a first tier broadband communication interface and a second tier narrowband communication interface. The first tier broadband communication interface provides the broadband link (120) and the second tier narrowband interface provides the IoT link (106). While the narrowband link may provide coverage of a comparatively large area at a reduced data rate that may be particularly suitable for tag sensors (104) and other sensors (122), the broadband link may provide coverage of a comparatively smaller area at a higher data rate that may be suitable to serve other devices such as laptops (130), smartphones (128), or other broadband equipment, including drones (118), cameras (not shown), etc. The broadband link may further be used to establish a mesh with other access points, as previously shown in FIG. 1B. In one embodiment of the invention, the monitoring system includes a three-tier network that, in addition to the two tiers of the access point, includes a third tier formed by the local sensor link (126), as previously described.

FIG. 1C further shows a radio frequency identification (RFID) wand. The RFID wand may be used, e.g., by a rancher in proximity of a monitored animal (102) that is equipped with an RFID transmitter to read out basic information about the animal. The RFID transmitter may be a component of the tag sensor (104) or of the in-vivo sensor (124) and may provide static information such an animal-specific ID. The RFID wand may be equipped with a GPS unit, enabling obtaining a location at the time when RFID information is obtained from an animal. Additionally or alternatively, the RFID wand may be equipped with an IoT interface enabling the RFID wand (132) to communicate with one or more access points (112) in order to obtain a location and/or to upload RFID information obtained from an animal. Further, RFID wands, in accordance with one or more embodiments of the invention, may be equipped with a narrowband communication interface to establish a narrowband link (136), e.g., a Bluetooth link to another device such as a smartphone (128) or a laptop (130). The narrowband link may enable a user to access RFID data either spontaneously, e.g. as an RFID transmitter is read, or in bulk readouts, after a number of RFID transmitters have been scanned.

Figure 1D:
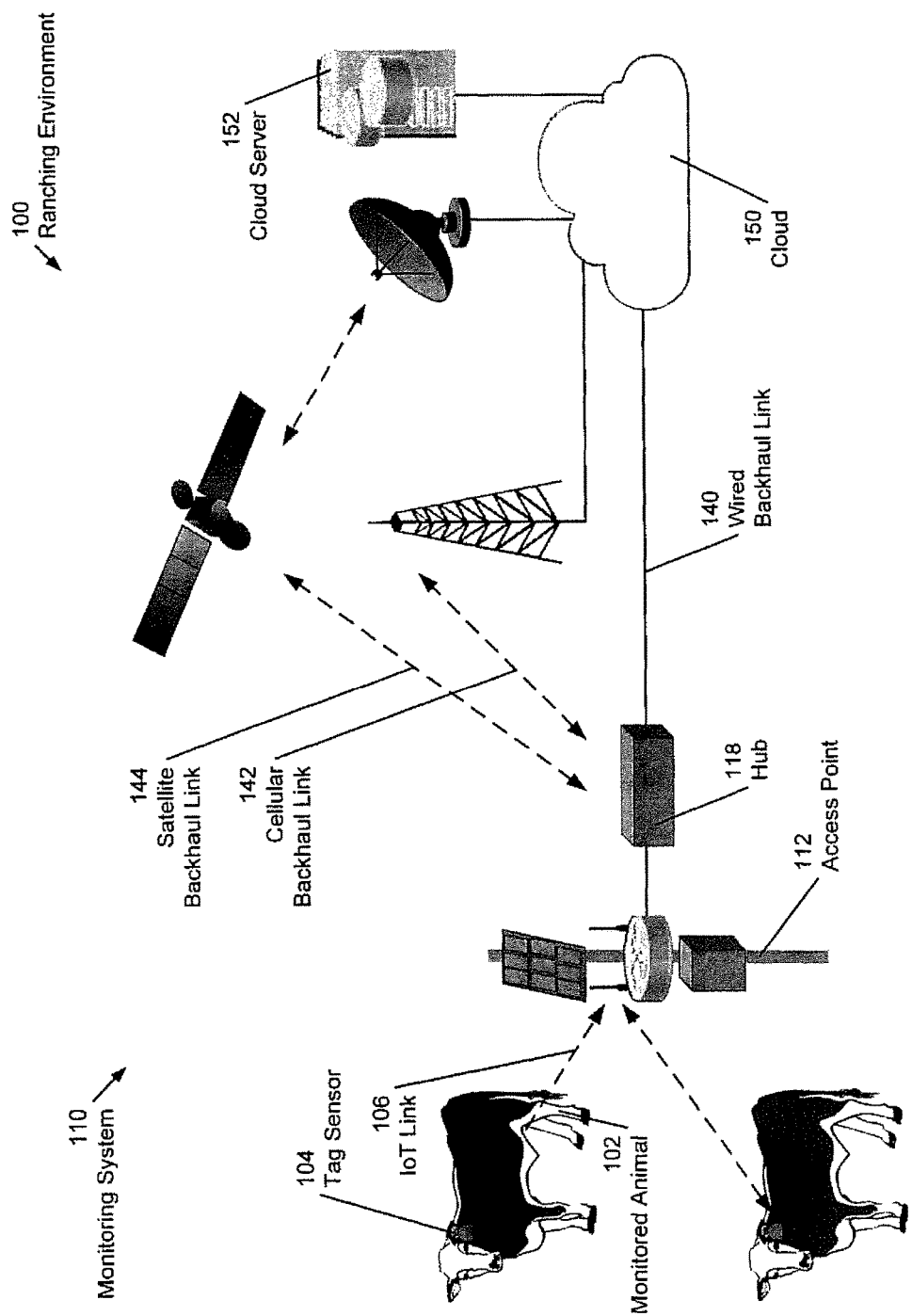

Turning to FIG. 1D, various options for interfacing the hub (118) with the computing devices in the cloud (150), e.g., using the Internet, are illustrated, in accordance with one or more embodiments of the invention. A wired backhaul uplink (140), a cellular backhaul uplink (142) and/or a satellite backhaul uplink may be used to interface the hub (118) with a cloud computing device, e.g., the cloud server (152). Alternatively, any other data connection, including any kind of point-to-point or multipoint connection that is at least temporarily available may be used as a backhaul link. In one embodiment of the invention, no backhaul link is used, i.e., the hub (118) is operating without an interface to the cloud (150), and therefore may only be accessed using local computing devices accessing the hub (118) via the access point (112), as previously described with reference to FIG. 1C. Alternatively, in one embodiment of the invention, no hub is used, i.e., the access point(s) may be directly connected to the backhaul link. Such a configuration may be suitable if the backhaul link is considered very reliable. Alternatively, if the backhaul link is considered less reliable, the hub may provide full or at least partial functionality while the cloud is not reachable.

The wired backhaul link (140) may be, for example, a wired Ethernet connection to an Internet service provider, a fiber-optic connection, a DSL Internet connection, a cable Internet connection, etc. Any type of wired data interface suitable to connect the hub to the cloud environment (150) may be used. The cellular backhaul link may be any type of cellular data connection such as a 3G, LTE or 5G data connection. Those skilled in the art will appreciate that any type of wired or wireless data link may be used as a backhaul link, without departing from the invention.

Turning to FIG. 1E, an exemplary radio signal coverage by a single access point (112), in accordance with one or more embodiments of the invention, is shown. As illustrated, a smaller region surrounding the access point receives broadband coverage (dashed circle), e.g., via the Wi-Fi signal of the access point. Within this zone, sensors that require a broadband link, e.g. cameras, may be installed. A larger region, surrounding the access point, receives narrowband coverage by the IoT link (108) (solid circle). While less data may be transmitted using the IoT link, data transmission using the IoT link may require less power and may be feasible over longer distances, in comparison to the broadband link. A tag sensor (104), which is typically battery-powered, therefore may use the IoT link rather than the broadband link. Those skilled in the art may appreciate that the areas that receive broadband and narrowband coverage depend on various factors, including the transmission power of the components involved in data transmissions, the types of antennas being used, terrain features, etc.

Figure 1F:
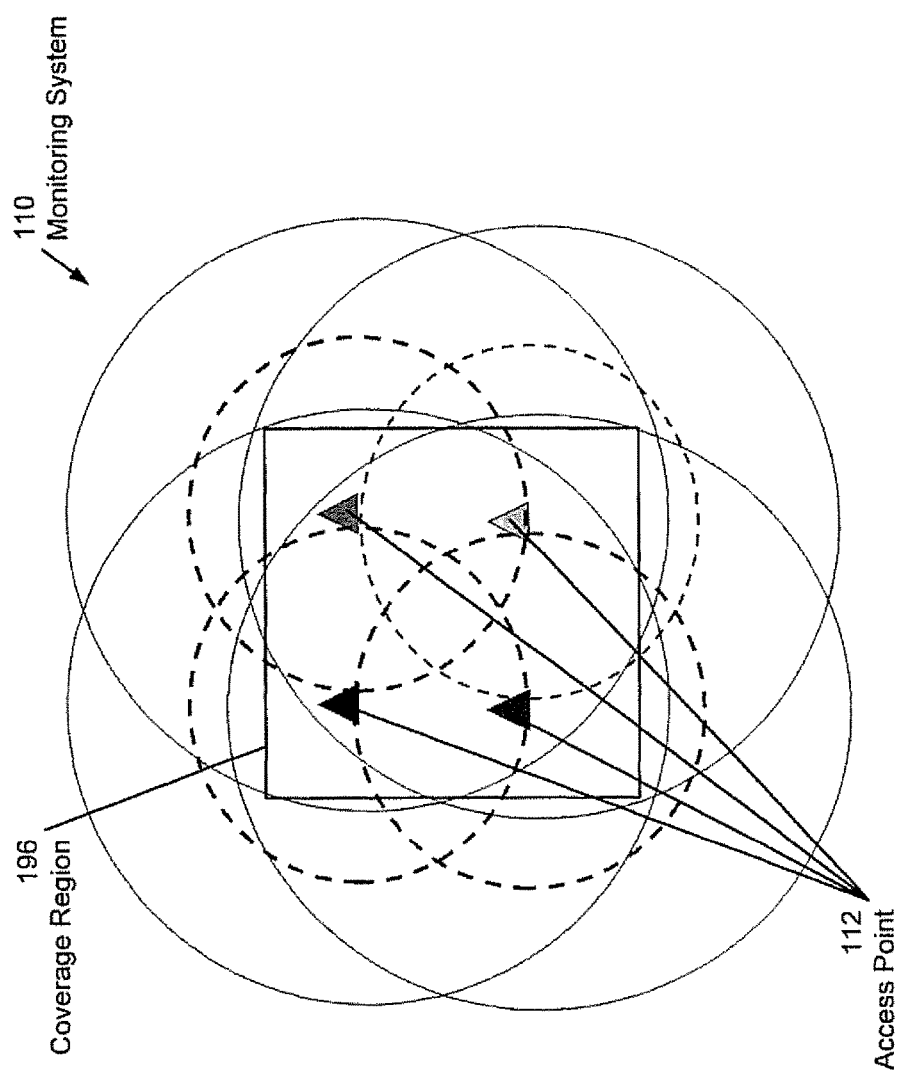

Turning to FIG. 1F, an exemplary radio signal coverage by multiple access points (112), in accordance with one or more embodiments of the invention, is shown. In the shown configuration, the access points are spaced such that there is significant overlap between the broadband coverage (dashed circles) provided by the different access points, but also between the narrowband coverage (solid circles) provided by the different access points. Using the set of access points, a coverage region (196) is entirely covered by narrowband signals of at least three access points. In one or more embodiments of the invention, overlap of narrowband coverage provided by multiple access points is desirable. Specifically, in a region where a sensor receives narrowband coverage by at least three narrowband signals (e.g., IoT signals), the signals of a device (e.g., a tag sensor), received by at least three access points may be used to determine the location of the sensor, thus enabling, for example, location tracking of an animal equipped with a tag sensor. The location of a sensor may be determined using time difference of arrival (TDOA) methods. Accordingly, location tracking using TDOA methods may be performed in the coverage region (196) in which at least three access points may receive transmissions sent by the device. TDOA positioning may provide moderately accurate location information (e.g. with an accuracy of approximately 30-75 m) and the accuracy may deteriorate when the quality of the reception at one or more of the access points is poor. The measurement accuracy may, however, not be strongly affected by the presence of buildings and foliage. Alternatively, received signal strength indication (RSSI) positioning may provide location information with limited accuracy, (frequently no more accurate than approximately 75 m), and may allow positioning even under difficult conditions, e.g., when fewer than three access points are available. Further, if equipped with a global positioning system (GPS) receiver, the device location may be determined using the GPS receiver. GPS positioning does not rely on the exchange of signals with access points and may thus be available anywhere, even outside the coverage region (196), although power requirements may be significantly higher when relying on GPS. Further, GPS signals may be blocked by structures, foliage, etc. However, the accuracy is typically higher than the accuracy of the TDOA and RSSI methods.

Accordingly, to enable energy efficient location determination in certain regions, access points may be strategically placed to have overlapping coverage regions, thereby not requiring the use of power consuming GPS positioning. In regions where TDOA based location services are desired, a dense grid of access points with a high degree of overlap may be installed to ensure that overlapping coverage is provided by at least three access points, whereas a sparse grid of access points may be installed in other regions. In these other regions, less accurate RSSI positioning may be used, or if an accurate location is required, GPS positioning may be used.

Figure 1G:
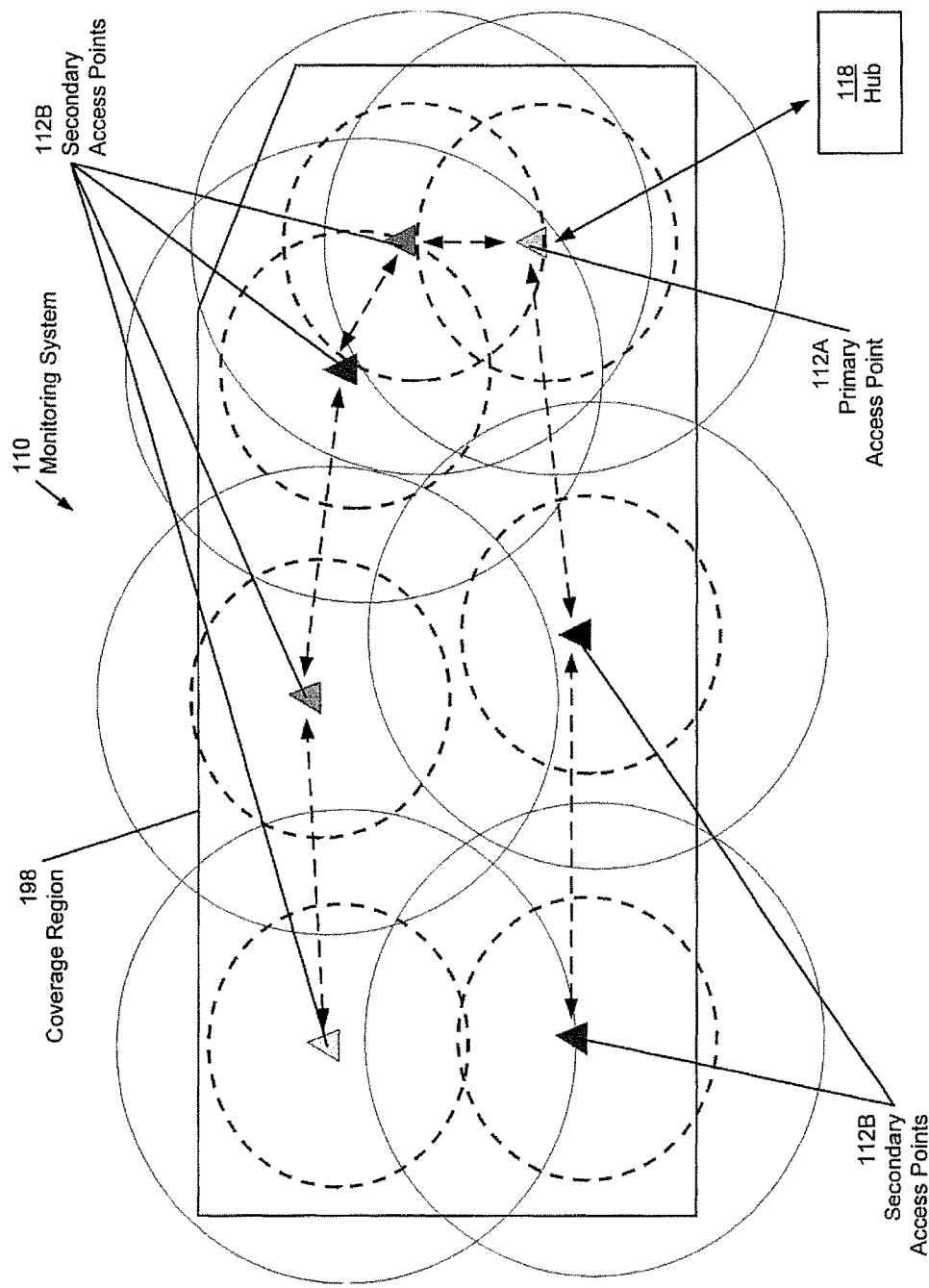

Turning to FIG. 1G, an exemplary radio signal coverage by multiple access points (112A, 112B), in accordance with one or more embodiments of the invention, is shown. To cover large areas effectively while allowing for extended battery life, up to years, access points may need to be deployed strategically to cover the ranch or farmland area. The configuration shown in FIG. 1G uses a primary access point (112A) that directly interfaces with a hub (118) and provides an interface to the secondary access points (112B). Using the set of access points, a coverage region (198) is entirely covered by a narrowband signal (solid circles), while some areas are also covered by a broadband signal (dashed circles). In the exemplary configuration shown in FIG. 1G, the left part of the coverage region (198) is covered by sparsely placed access points, where broadband coverage regions are non-overlapping. In contrast, the right part of the coverage region (198) is covered by densely placed access points, where broadband coverage is overlapping, thus establishing a contiguous region with broadband signal coverage. Those areas may, thus, serve different purposes. For example, the left part may be used to monitor sensors that merely require a narrowband communication interface, e.g., weather sensors or tag sensors of animals for which no TDOA tracking is necessary. In contrast, the right part may be used for a drone surveillance that requires a continuous broadband signal. Those skilled in the art will appreciate that even though FIG. 1G shows the primary access point (112A) interfacing with a hub (118), the hub is not necessarily required. For example, the primary access point (112A) may directly interface with the cloud environment (150). Further, to provide coverage for larger areas and/or for larger numbers of animals, additional access points, including primary and/or secondary access points and/or additional hubs may be deployed.

Figure 1H:
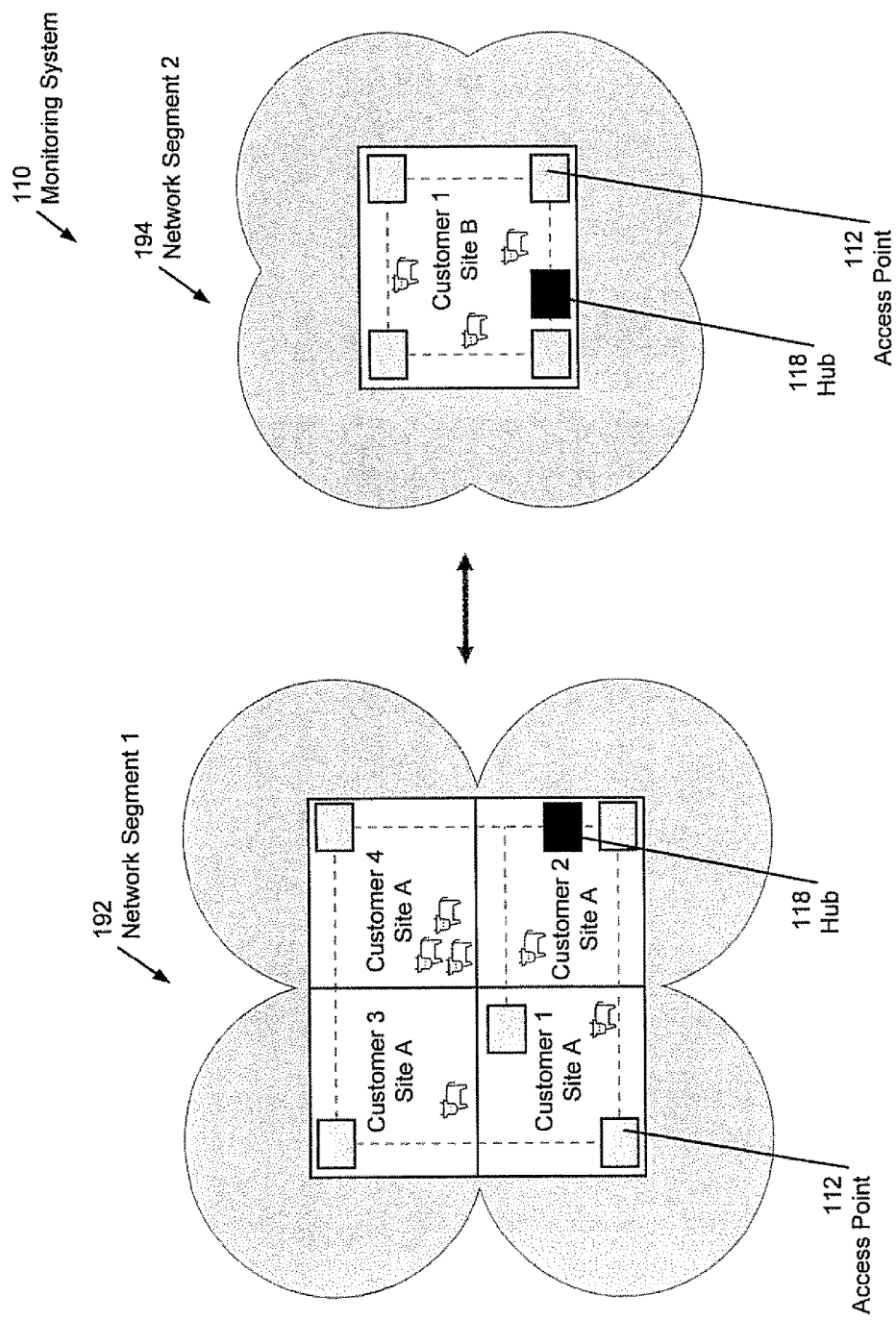

Turning to FIG. 1H, an exemplary monitoring system (110) that includes multiple network segments (192, 194), in accordance with one or more embodiments of the invention, is shown. Each of the network segments (192, 194), is equipped with a hub (118) and multiple access points (112), providing coverage for the monitoring of livestock. Alternatively, these network segments may be operated without hubs. Further, both network segments operate using the same RF plan, i.e., using the same transmission protocol and frequencies, further described in FIG. 6. Network segment 1 (192) is configured as a multitenant site, i.e., multiple customers are served by the network segment. Consider, for example, a monitoring system (110) that is installed in a rural area by a provider that offers the monitoring of livestock as a service. Multiple ranchers (customers 1-4, shown in FIG. 1H) sign up for the service and have their animals monitored by the monitoring system. The monitoring system may be publicly or privately operated. The animals may be kept separate (e.g. in fenced separate areas) or they may be kept in a larger combined area. Optionally, the animals may freely move across sites within the area but trigger a notification or an alarm if detected in a location different from the rancher's site, to let the rancher know that animals have left his property. One of the ranchers (customer 1) owns additional land (site B) that is separate from site A. This additional land is also used for raising livestock and is monitored by an additional network segment. Network segment 2 may or may not use the same RF plan as network segment 1. Because network segments 1 and 2 belong to the same monitoring system, information about devices may be exchanged between the network segments. Accordingly, moving animals from site A to site B is straightforward. The scenario of FIG. 1H thus illustrates a multitenant, multisite monitoring system, in accordance with one or more embodiments of the invention. Those skilled in the art will appreciate that monitoring systems, in accordance with one or more embodiments of the invention, are fully scalable. For example, monitoring systems may include any number of sites, any number of customers and any number of animals being monitored. Further, monitoring systems, in accordance with one or more embodiments of the invention, may be globally distributed. For example, sites A and B may be on different continents. Network segments may grow arbitrarily large, with any number of access points and/or tag sensors or other monitored devices. However, eventually a network segment with numerous devices may become congested, or the hub of the network segment may be overwhelmed by the incoming volume of data. In such a scenario, the network segment may be split into two or more separate network segments, each with its own hub and access points.

Figure 2A:
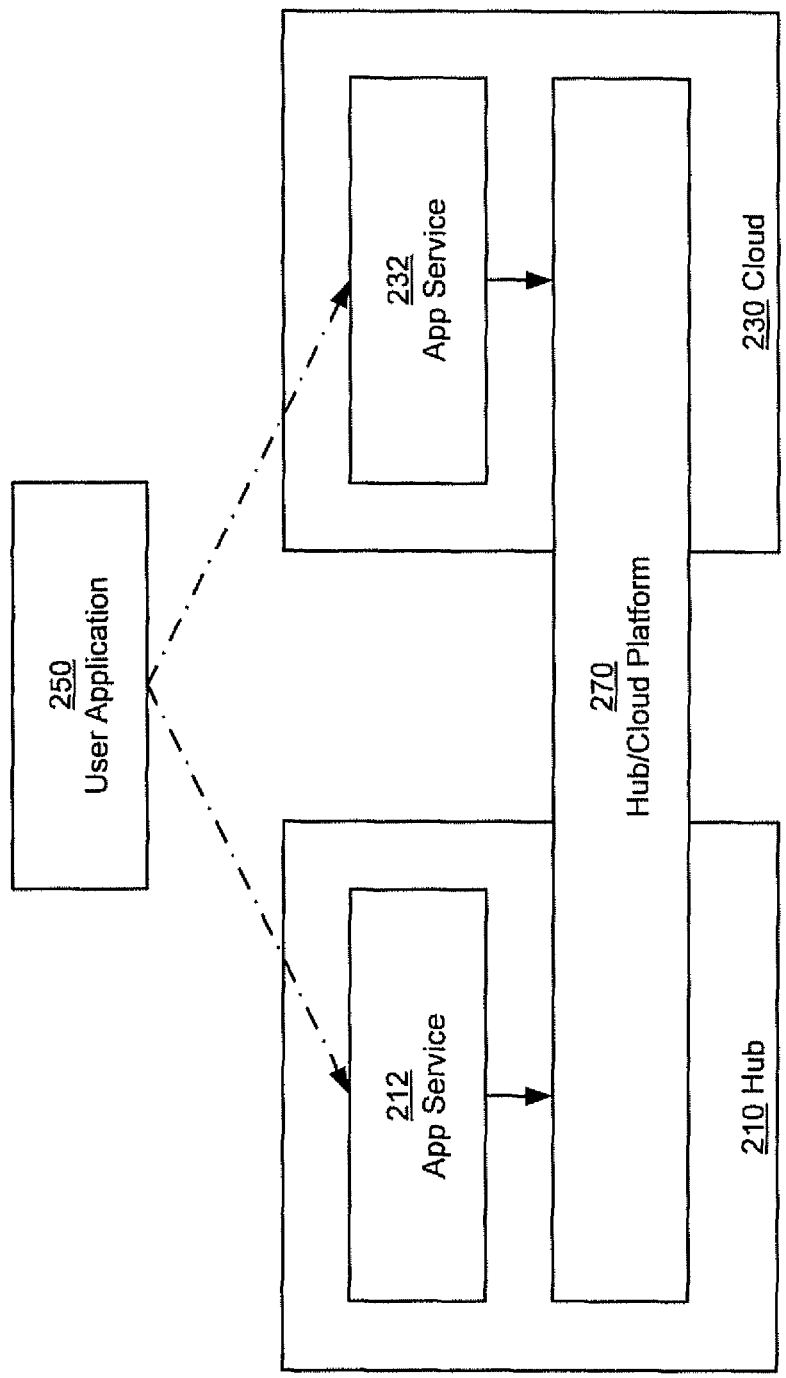
FIGS. 2A and 2B show a hub-cloud configuration of a system for monitoring livestock, in accordance with one or more embodiments of the invention.

Turning to FIG. 2A, a hub-cloud configuration of a system for monitoring livestock, in accordance with one or more embodiments of the invention, is shown. The hub-cloud configuration includes the hub (210), the cloud (230), and the user application (250). A hub/cloud platform (270), jointly executing on the hub (270) and in the cloud (230) in a distributed manner, provides back end-support for various components of the monitoring system (110), as further described with reference to FIG. 2B. A user application (250) may be relied upon by a user to access the hub/cloud platform (270) via the hub (210) and/or via the cloud (230). Each of these components is subsequently described.

Services, made available through the hub/cloud platform (270) may include, for example, providing data, gathered by the monitoring system (110), to the user, enabling the user to configure the monitoring system, etc. The hub/cloud platform (270) may be accessed by a user using the user application (250), which may be executing on a computing device such as a smartphone or a laptop. The user application (250), thus, may provide a user interface configured to enable the user to access the hub/cloud platform, and to receive notifications on critical events. The user application may include, for example, alert displays, status messages, data visualization capabilities, control and configuration capabilities, etc. The user application may further provide data entry fields (e.g., to configure the monitoring system), specialized control interfaces (e.g., to control a drone), voice over IP (VoIP) and/or push to talk interfaces and other communication interfaces that are supported by the broadband links provided by the access points. Alternative implementations of the user application (250) may operate on other devices, e.g., on an audio alert device.

Depending on whether the user application (250) accesses the hub/cloud platform (270) via the hub (210) or via the cloud (230), the user application (250) may interface with the hub/cloud platform via the app service (212) of the hub (210) (e.g., using a smartphone's Wi-Fi interface) or via the app service (232) of the cloud (230) (e.g., using the smartphone's LTE interface). When a user is on-site, e.g., directly connected to an access point using a Wi-Fi link, accessing the hub/cloud platform (270) may be particularly low-latency because the interaction of the user's computing device with the hub is local.

The hub (210), includes a computing device configured to perform at least some of the steps described with reference to the flowcharts of FIG. 8, and one or more communication interfaces that enable the hub to interface with one or more access points (112), the cloud (230), and the computing device that executes the user application (250). The computing device of the hub may be, for example, an embedded system that includes all components of the computing device on a single printed circuit board (PCB), or a system on a chip (SOC), i.e., an integrated circuit (IC) that integrates all components of the computing device into a single chip. The computing device may include one or more processor cores, associated memory (e.g., random access memory (RAM), cache memory, flash memory, etc.), one or more network interfaces (e.g., an Ethernet interface, a Wi-Fi interface, a Bluetooth interface, etc.), and interfaces to storage devices, input and output devices, etc. The computing device may further include one or more storage device(s) (e.g., a hard disk, an optical drive such as a compact disk (CD) drive or digital versatile disk (DVD) drive, flash memory, etc.), and numerous other elements and functionalities. In one embodiment of the invention, the computing device includes an operating system that may include functionality to execute the methods further described below. Those skilled in the art will appreciate that the invention is not limited to the aforementioned configuration of the computing device.

Figure 7:
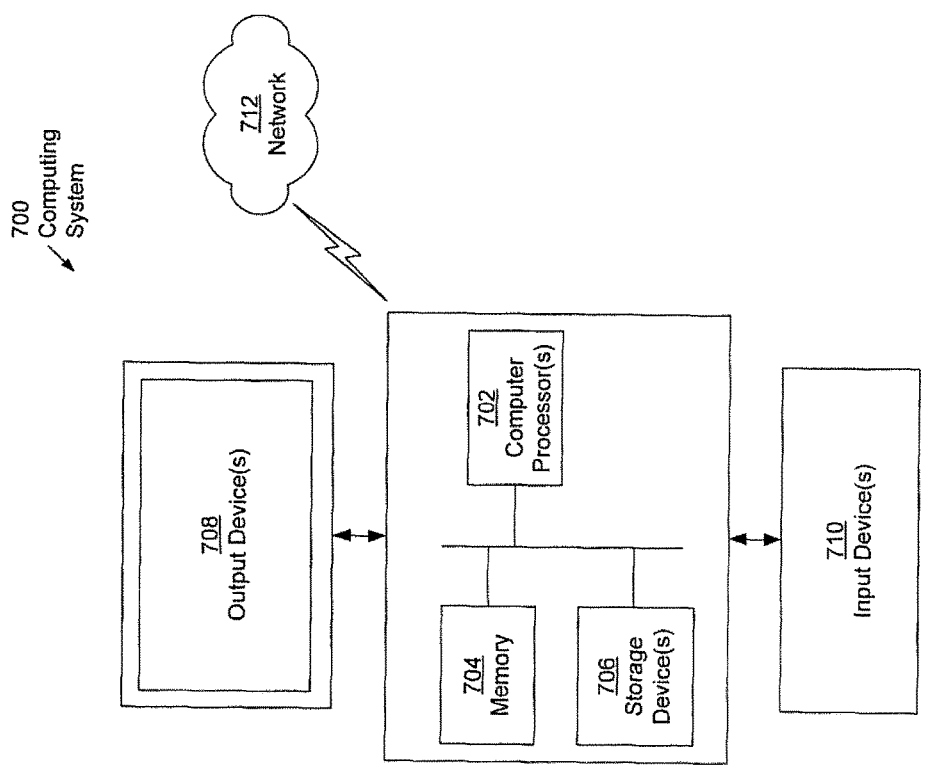
FIG. 7 shows a computing system in accordance with one or more embodiments of the invention.

The cloud (230), in accordance with one or more embodiments of the invention, may be formed by multiple/many networked computing devices. These computing devices may be geographically and organizationally distributed in any way. For example, some of these computing devices may be located in a data center, whereas other such computing devices may be individual physical or virtual servers. An exemplary computing system, as it may be used in the cloud, is shown in FIG. 7. One or more of the computing devices may host the hub/cloud platform (270), analogous to how the hub/cloud platform is hosted on the hub (210). While the components of the hub/cloud platform that are executing on the hub (210) and that are executing on a computing device in the cloud (230) may operate separately, they are interconnected, e.g. via the backhaul link (140), thus enabling synchronization between these components. Accordingly, the same information may be available, regardless of whether the user application connects via the hub (210) or via the cloud (230). Temporary discrepancies may exist though, e.g., during times when the backhaul link (140) is interrupted, and a synchronization is therefore unavailable. Further, because additional, e.g., more complex, data processing may be performed in the cloud, additional data, resulting from the additional processing, may be available when connecting to the hub/cloud platform (270) via the cloud. Such data may, however, also be available via the hub (210), if they are synchronized to the hub (210) via the backhaul link (140). The cloud may run multiple instances of the hub/cloud platform in order to support the load of many sites and/or many users. Depending on the configuration of the hub/cloud platform, incoming data, i.e., data received from a particular hub, a particular device, a particular site, or a particular customer, may be distributed between multiple instances, or may be consistently assigned to the same instance, using, e.g., a consistent hash ring configuration.

Those skilled in the art will recognize that other configurations that deviate from the configuration introduced in FIG. 2A may exist, without departing from the invention. For example, in monitoring systems (110) that do not include an interface to the cloud (230), the hub/cloud platform (270) may solely execute on the hub. In such a scenario, the hub is configured to "self-backhaul", i.e., the hub may collect and consolidate sensor data and may perform some or even all of the processing that would otherwise be performed in the cloud. Similarly, in monitoring systems in which the access points (112) directly interface with the cloud (230), the hub/cloud platform (270) may solely execute in the cloud. All functionality, even functionally that would typically be provided by the hub, in this case may be provided in the cloud. The configuration of the monitoring system, with or without hub, in one or more embodiments of the invention, may be transparent, i.e., sensors or other devices may operate in the same manner, regardless of the presence of a hub. Similarly, a user may experience the same monitoring system, whether the hub is present or not.

Figure 2B:
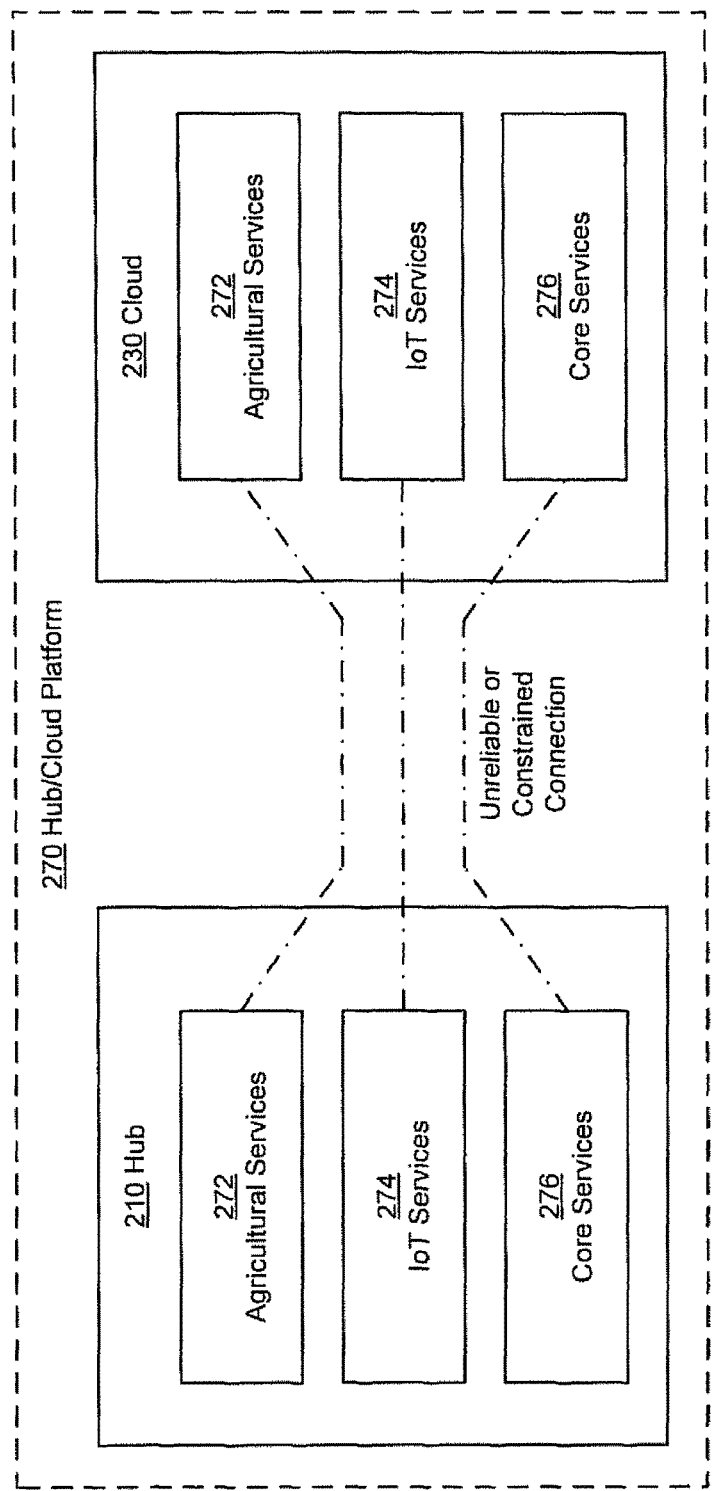

Turning to FIG. 2B, additional details of the hub/cloud platform (270) are shown. In one or more embodiments of the invention, the hub-cloud platform is organized in layers. Core services (276) provide basic functionalities such as data storage, network, and messaging. On top of the core services (276), the IoT services (274) provide services that are specific to IoT networks, but that are not necessarily specific to a particular application, such as the use in an agricultural environment. The IoT services, may thus include, for example, location services (e.g., GPS, TDOA or RSSI based), IoT network services and configurations, etc. The topmost layer includes agricultural services (272). These agricultural services may include, for example, behavioral analytics that are used to monitor the well-being of the livestock. Additional application-specific layers may be added, without departing from the invention.

These services, in accordance with one or more embodiments of the invention, may be available through the hub (210) and/or through the cloud (230). A synchronization may be performed between the services executing in the cloud and the services executing on the hub, thus maintaining consistency between the hub and the cloud. As long as a communication link (e.g., the backhaul link (140)) is available, the data available through the hub and through the cloud may be identical. However, if the communication link temporarily becomes unavailable, data that are accumulated on the hub may not be available through the cloud. A synchronization may be performed once the communication link is restored, to update the cloud with the data available on the hub. Accordingly, a consistent data view is available via hub and cloud, in accordance with one or more embodiments of the invention.

Figure 3B:
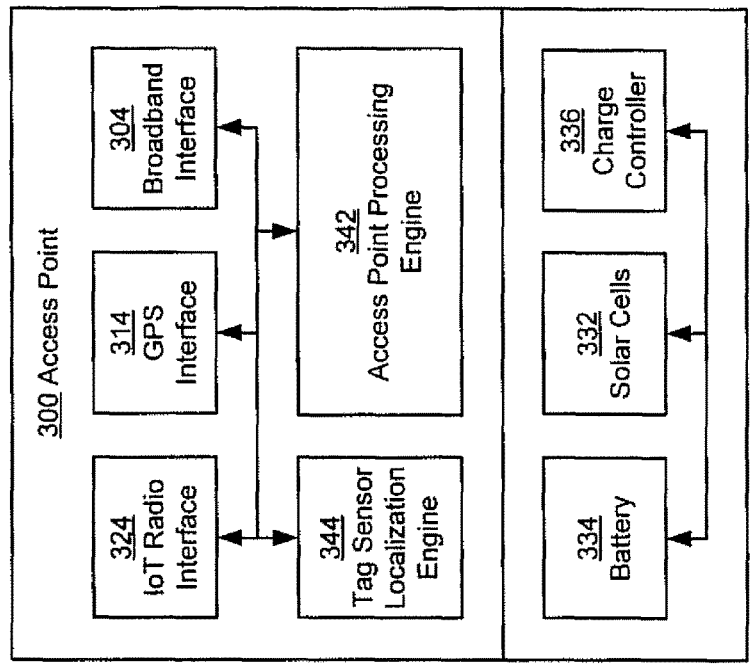
Figure 3A:
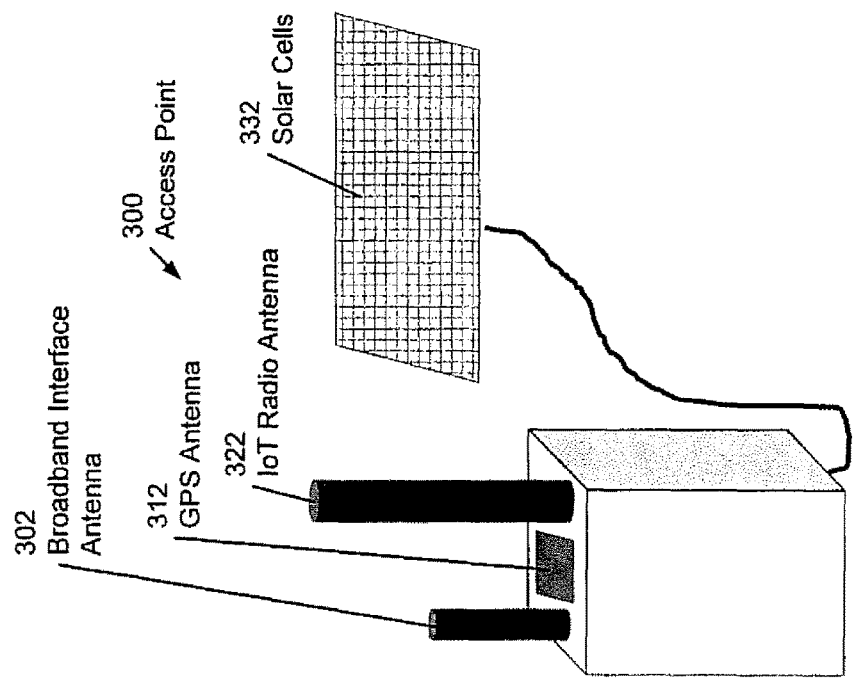

Turning to FIGS. 3A and 3B, access points (300), in accordance with one or more embodiments of the invention, are shown. In FIG. 3A, the general design of an exemplary access point is shown, and in FIG. 3B, the architecture of the access point is illustrated. The exemplary access point shown in FIG. 3A includes a broadband interface antenna (302), a GPS antenna (312), an IoT radio antenna (322) and solar cells (332). As shown in FIG. 3B, the access point further includes a broadband interface (304), a GPS interface (314) and an IoT radio interface (324).

The broadband interface (304) uses the broadband antenna (302) in order to send and receive broadband data transmissions when in contact with, e.g., other access points, as illustrated in FIG. 1B and/or with other devices such as smartphones, laptops, cameras and/or drones that are also equipped with broadband interfaces. The broadband interface may support mesh, point-to-point and multi-point connections. The broadband interface may be a WLAN interface based on the Wi-Fi standard, using, e.g., the 2.4 and/or 5 GHz radio bands. Alternatively, the broadband interface may be a cellular data interface, e.g., a 3G or 4G/LTE or 5G interface, or any other wireless data interface, without departing from the invention.

The GPS interface (314) uses the GPS antenna (312) to obtain position signals from the global positioning system or from alternative satellite navigation services. The position signal enables the access point to accurately determine its own position. In one or more embodiments of the invention, the GPS interface further obtains an accurate time base that may be used by the access point to perform localization tasks using TDOA methods, as further described below.

The IoT radio interface (324) uses the IoT radio antenna (322) to communicate with one or more IoT devices such as the tag sensors (104). The IoT interface may be based on a low power wide area network standard such as, for example, LoRa. The resulting narrowband link is particularly suitable for communications between the access point and the tag sensors or other sensors, due to its low power requirements, long range, and its ability to interface with many tag sensors and/or other devices. In one or more embodiments of the invention, the IoT radio interface (324) supports communication protocol extensions implemented on top of an existing IoT communication protocol to provide scheduled communications and timing beacons as further discussed below, with reference to FIG. 6.

In one or more embodiments of the invention, the access point (300) further includes an access point processing engine (342). The access point processing engine may handle the processing of data received from devices, such as tag sensors, and may coordinate the uploading of the processed data to either the hub or to the cloud. The processing of data may involve, for example, data aggregation, data filtering, data fusion, data compression and/or data encryption.

Figure 6:
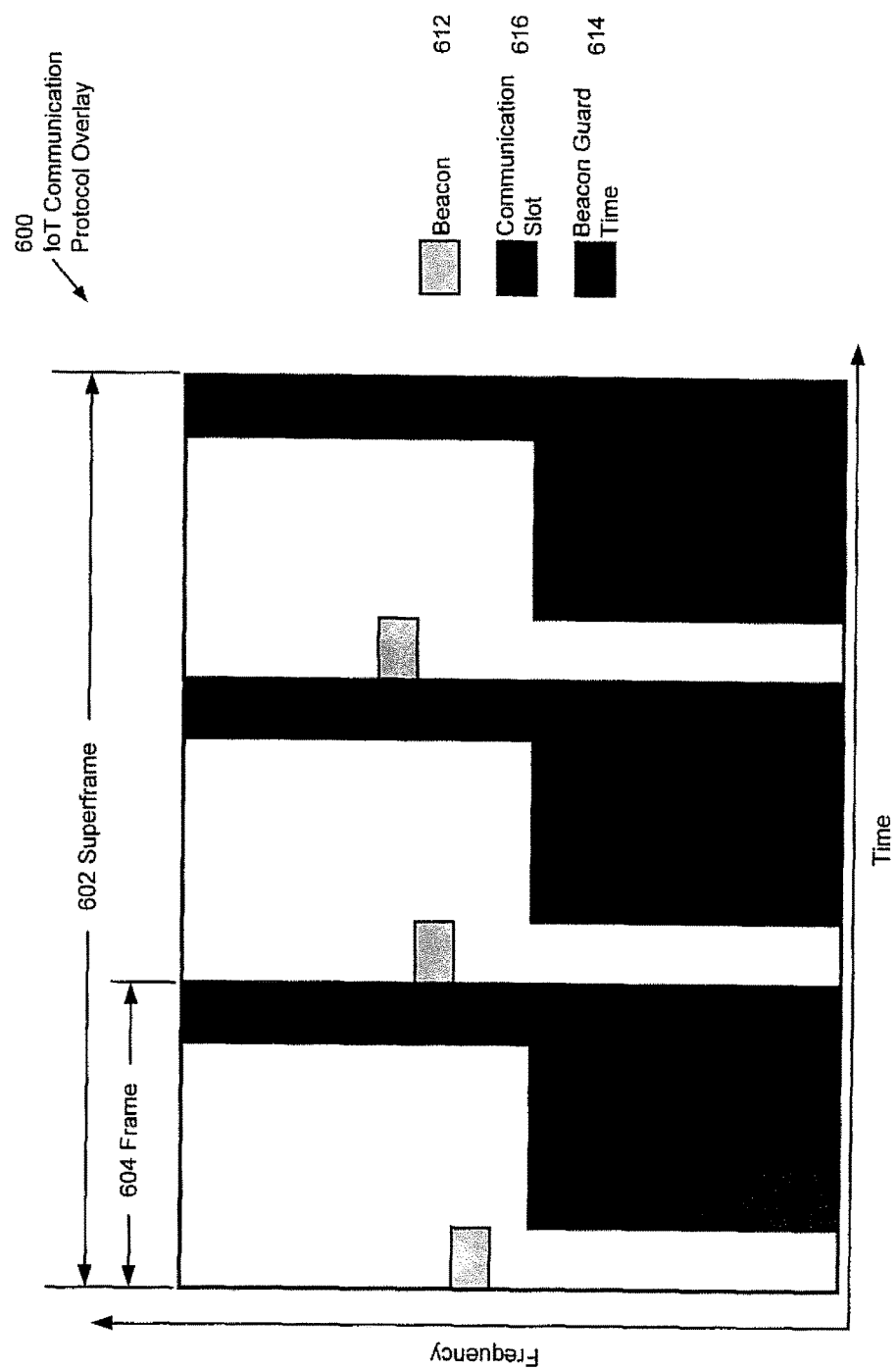
FIG. 6 shows an Internet of Things (IoT) communication protocol overlay, in accordance with one or more embodiments of the invention.

In one or more embodiments of the invention, the access point (300) further includes a tag sensor localization engine (344). The tag sensor localization engine may be used to determine the locations of tag sensors that are within the coverage region of the access point. The localization may be performed, for example, using TDOA methods. Using the TDOA method, triangulation, based on the differences in time delay of a data transmission by a tag sensor, received by at least three access points, may be performed. The tag sensor localization engine of an access point may use this time delay information to determine the location of the tag sensor responsible for the data transmission. Because TDOA methods depend on the availability of an accurate time base to the tag sensors whose location is to be determined, communication protocol extensions that enable dissemination of an accurate time base to the tag sensors (and other sensors) via the IoT link, as discussed with reference to FIG. 6, are used by the access point. Alternatively, the tag sensor localization engine may extract the location of a tag sensor from a message provided by a sensor equipped with a GPS unit. Further, the tag sensor localization engine may also determine a location of a tag sensor based on the signal strength of a data transmission obtained from the tag sensor, using the RSSI method. Those skilled in the art will appreciate that, although the method performed by the tag sensor localization engine is described with regard to tag sensors, any device that is equipped with an IoT interface, and that is capable to communicate with the access points, may be localized by the tag sensor localization engine.

The access point processing engine (342) and the tag sensor localization engine (344) may be software executing on a computing device (not shown) of the access point (300). The computing device of the hub may be, for example, an embedded system that includes all components of the computing device on a single printed circuit board (PCB), or a system on a chip (SOC), i.e., an integrated circuit (IC) that integrates all components of the computing device into a single chip. The computing device may include one or more processor cores, associated memory (e.g., random access memory (RAM), cache memory, flash memory, etc.), and interfaces to storage devices, input and output devices, etc. The computing device may further include one or more storage device(s) (e.g., a hard disk, an optical drive such as a compact disk (CD) drive or digital versatile disk (DVD) drive, flash memory, etc.), and numerous other elements and functionalities. In one embodiment of the invention, the computing device includes an operating system that may include functionality to execute the methods further described below. Those skilled in the art will appreciate that the invention is not limited to the aforementioned configuration of the computing device.

In one or more embodiments of the invention, the access point further includes a power system that may include the solar cells (332), a battery (334) and a charge controller (336), powering the access point. The battery may be deep-cycle capable to guarantee continued operation at night or under cloudy conditions when power provided by the solar cells is insufficient. The solar cells may be dimensioned to enable powering the access point while also recharging the battery. Alternatively, the access point may be powered externally, e.g., using power over Ethernet (PoE) or using a dedicated power input. The charge controller in combination with the access point processing engine (342) may provide charging, battery status and power consumption analytics, enabling power management of the access point. A direct current (DC) power and data over DC power link may be used to power the access point by the power system, but also to enable the charge controller to communicate status information (such as battery level, temperature, etc.) to the access point.

Figure 4A:
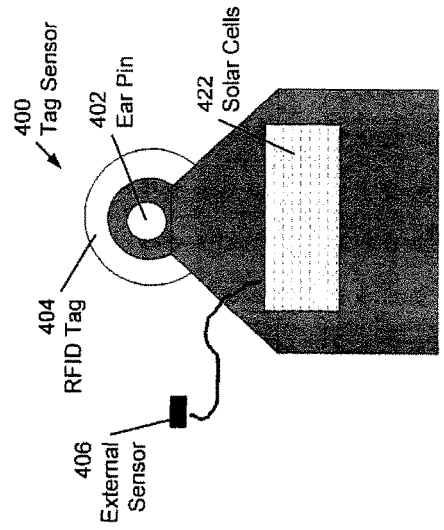
FIGS. 4A-4C show tag sensors of a system for monitoring livestock, in accordance with one or more embodiments of the invention.
Figure 4B:
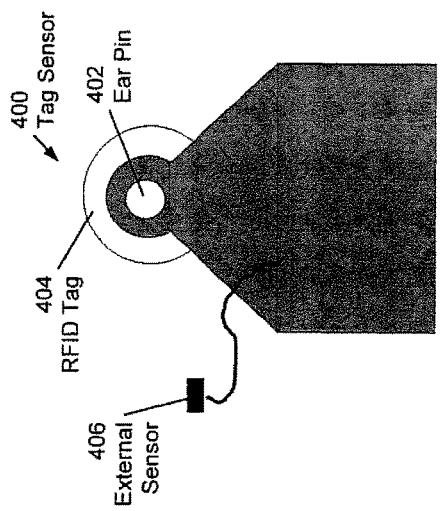
Figure 4C:
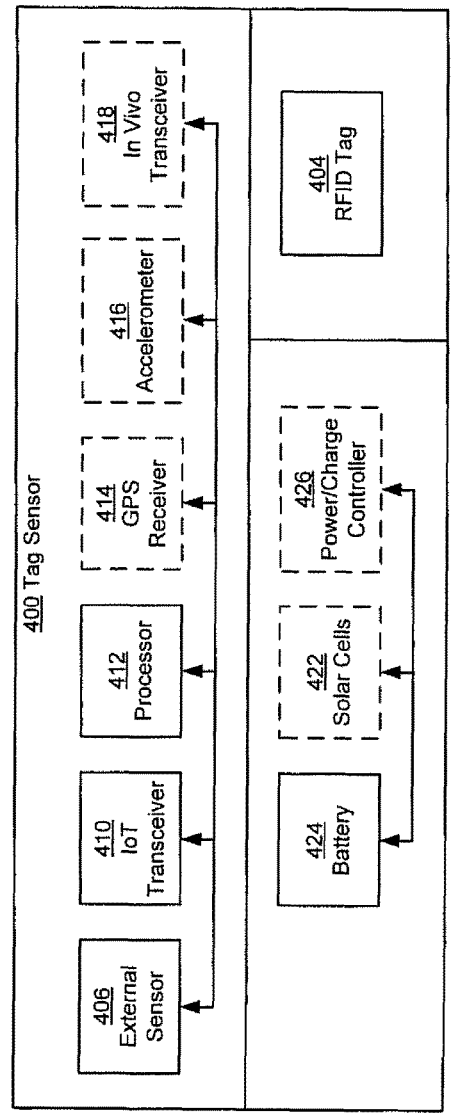

FIGS. 3C-3G show an exemplary access point & hub assembly, in which a hub and an access point are installed in combination on a pole. The assembly (390) includes the access point (300), an antenna pole (392), solar cells (332) and a hub & battery box (394). While the access point (300) is installed near the top of the antenna pole (392), for improved reception, the hub (318) may be housed in the hub & battery box (394), together with the battery (334) and the charge controller (336) near the base of the antenna pole (392), thus facilitating access. The access point (300) may be connected to the hub (318), using an Ethernet cable, which may also power the access point using PoE. In one embodiment of the invention, the antenna pole (392) can be pivoted into a horizontal position, thereby facilitating installation and servicing of the access point (300) near the top of the antenna pole as illustrated in FIG. 3G FIGS. 4A-4C show tag sensors (400) in accordance with one or more embodiments of the invention. While FIGS. 4A and 4B show an exemplary design of the tag sensor, FIG. 4C show the functional structure of an exemplary tag sensor. A tag sensor may be used to monitor an animal, including the animal's location and other variables, as subsequently discussed. The tag sensor may be equipped with a fastener such as an ear pin (402) that allows the tag sensor to remain attached to the animal for a prolonged time, up to multiple years. Other designs may not include an ear pin. For example, alternatively, the tag may be integrated in a collar worn by the animal. The tag sensor may further be equipped with an RFID tag. The RFID tag may electronically store information such as a unique animal-specific identifier. The RFID tag may be passive, i.e., not requiring a battery, and may be electromagnetically powered by a nearby reader, e.g., the RFID wand (132), previously discussed in FIG. 1C. The tag sensor may further include active components, including one or more external sensors (406). Data from these sensors may be transmitted to one or more of the previously introduced access points using an IoT link. The external sensors may be physiological sensors that may have a wired or optical interface (e.g., infrared) to the tag sensor. Sensors may include, but are not limited to animal temperature, ambient temperature, pulse rate and blood pressure sensors. The animal temperature may be obtained using, for example, a temperature probe inserted into an animal's ear canal. The ambient temperature may be obtained using, for example, the temperature sensor of the processor (412), or a dedicated temperature sensor. Further, heart rate and/or blood pressure may be assessed using LED light sources and photo sensors. Additionally or alternatively, other types of sensors may be integrated in a tag sensor (400). Any sensor that can be interfaced with the processor (412) using an analog or digital interface may be added to the tag sensor.

In one or more embodiments of the invention, the tag sensor (400) includes an IoT transceiver (410). The IoT transceiver (410) may be configured to communicate with one or more access points, using an IoT protocol such as LoRa. Communications may include, but are not limited to, the receiving of a time base from one or more access points, the receiving of a configuration, the receiving of a firmware, the sending of tag sensor data, e.g., data previously collected by one of the subsequently described sensors, and/or the sending of tag sensor status data, such as errors, battery level, etc. The activity of the IoT transceiver may be optimized to minimize power consumption. For example, the IoT transceiver may be in a deep sleep mode whenever no transmission of data is required.

In one or more embodiments of the invention, the tag sensor (400) further includes a processor (412). The processor may gather data from one or more of the subsequently described sensors and may process the data for transmission via the IoT transceiver. The transmissions may be performed as specified by the IoT communication protocol overlay, further described with reference to FIG. 6 to minimize communication inefficiencies such as collisions with data sent by other tag sensors and/or to conserve battery power. The organization of the data as instructed by the IoT communication protocol overlay may be performed by the processor (412). The processor may be a microcontroller unit (MCU) that may be implemented as a system on a chip (SOC). The processor may be selected based on computational requirements and battery life requirements.

In one embodiment of the invention, the tag sensor (400) may include a GPS receiver (414), an accelerometer (416) and/or an in-vivo transceiver (418). The GPS receiver, if present, may be used to determine the location of the animal when other, more power efficient, methods for determining the location (such as TDOA and/or RSSI) are not available, e.g., when the number of access points that are simultaneously in communication with the tag sensor is insufficient or the resulting location data are not sufficiently accurate. When not in use, the GPS receiver may be in a deep sleep mode or completely powered down. One or more accelerometers (416) may be used to track animal movements, such as head movements, which may indicate certain animal activity such as feeding. The accelerometer may be interfaced with the processor (412) using, for example, a digital interface. The optionally present in-vivo transceiver (418), in one embodiment of the invention, establishes a data link to an in-vivo sensor, such as a the in-vivo sensing capsule that is discussed below, with reference to FIGS. 5A and 5B. The data link may be very low power, limited to a range of only, for example, three to six feet. A transmission frequency may be in a range suitable to penetrate tissue. Highly power efficient circuits (such as class C amplification) may be used to minimize power consumption, in particular on the side of the in-vivo sensor, which may need to operate using small batteries. The data link may use a communication protocol analogous to the protocol further described below with reference to FIG. 6, although a simplified version (e.g., fewer communication slots) may be provided.

In one or more embodiments of the invention, the components of the tag sensor are battery powered. The battery (424) may be a rechargeable or a non-rechargeable battery that may or may not be replaceable, selected to power the components of the tag sensor for a specified duration, e.g., for multiple months or years. If the battery is rechargeable, a power or charge controller (426) may control the charging of the battery, e.g., from solar cells (422) or other external power sources, such as inductively provided power. The power/charge controller may further communicate battery status information to the processor (412). This status information may be communicated to an access point, e.g., when a low battery level is detected. In addition, the battery level may directly govern the operation of the sensor tag. For example, when a low battery level is detected, the communication frequency may be reduced, certain sensors may be deactivated, etc.

Figure 5A:
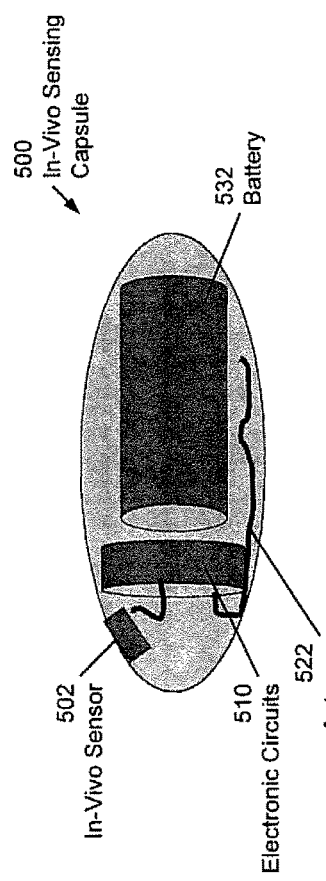
FIGS. 5A and 5B show in-vivo sensing capsules of a system for monitoring livestock, in accordance with one or more embodiments of the invention.
Figure 5B:
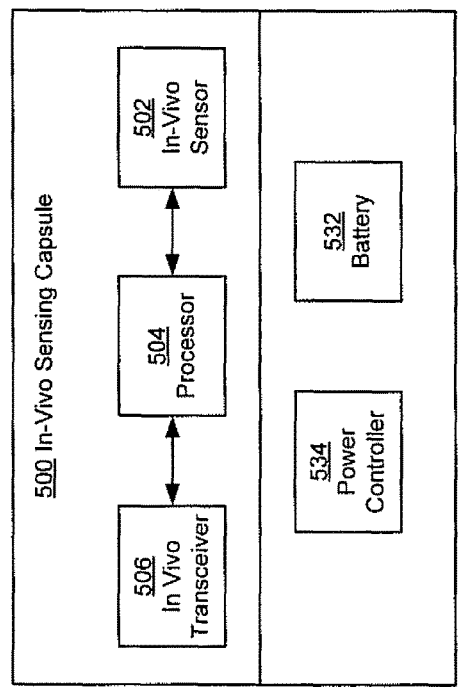

FIGS. 5A and 5B show in-vivo sensing capsules, in accordance with one or more embodiments of the invention. The in-vivo sensing capsule (500) may be an implanted capsule (e.g., a capsule that was subcutaneously injected) or an ingested capsule that is passing the digestive tract and may be used to collect physiological data. Other form-factors, such as dermal patches, may further be used, without departing from the invention. The in-vivo sensing capsule (500) may include an in-vivo sensor (502), electronic circuits (510), an antenna (522) and a battery (532). The in-vivo sensing capsule (400) may be hermetically sealed to prevent body fluids from entering the capsule. The capsule may be made from, for example, plastic, epoxy, ceramics or glass. The in-vivo sensor (502) may be a temperature sensor, a heart rate sensor, a blood pressure sensor, etc.

The electronic circuits (510), in accordance with one or more embodiments of the invention, includes a processor (504) and an in-vivo transceiver (506). The processor (504)

may be a particularly energy-efficient unit such as a microcontroller that may be implemented as a system on a chip (SOC). The processor may be selected based on computational requirements and battery life requirements. For example, an ingested in-vivo sensing capsule may only need to remain operative for a few days, whereas for an implanted version of the in-vivo sensing capsule it may be desirable to use the in-vivo sensing capsule for the lifetime of the animal. The in-vivo transceiver (506) is configured to interface the in-vivo sensing capsule with the tag sensor (400) over a short distance using a low-power signal with minimal power requirements, in order to communicate the collected physiological data to the tag sensor, from where it may be forwarded to an access point.

The battery (532) may be a rechargeable or a non-rechargeable battery, selected to power the components of the in-vivo sensing for a specified duration, ranging from a few days to the lifetime of the animal. If the battery is rechargeable, a power controller (534) may control the charging of the battery from inductively provided power. The power controller may further communicate battery status information to the processor (504). This status information may be communicated to an access point, e.g., when a low battery level is detected. In addition, the battery level may directly govern the operation of the in-vivo sensing capsule. For example, when a low battery level is detected, the communication frequency may be reduced, certain sensors may be deactivated, etc.

Turning to FIG. 6, an IoT communication protocol overlay, in accordance with one or more embodiments of the invention, is shown. The IoT communication protocol overlay is designed to enable the distribution of an accurate time base by an access point to tag sensors or other devices communicating with the access point. The IoT communication protocol overlay further establishes rules for data exchanges in the form of frequency bands and time slots to be used for communications, to reduce or eliminate collisions that may otherwise occur when multiple tag sensors attempt to simultaneously transmit data. In one or more embodiments of the invention, the IoT communication protocol overlay may be used to extend existing IoT protocols such as LoRa or SigFox, but also other protocols such as the 802.11 Wi-Fi protocol. FIG. 6 shows an IoT communication protocol overlay (600) in which a superframe (602) and frames (604) are established. The beginning of each frame is marked by a beacon (612), emitted by the access point. A beacon may include or may be followed by a communication of various data to the IoT devices within the range of the access point. The data may include a precise time base that the access point may have obtained from its GPS unit. The data may further include a specification of the IoT communication protocol overlay, thus informing the IoT devices that are supposed to communicate with the access point of the timing and frequency of time slots assigned to them for data transmission.

The beacon may then be followed by transmissions of sensor data in the communication slots (616). Each communication slot may be of a fixed duration and may be located at a set frequency. In the exemplary IoT communication protocol overlay (600) of FIG. 6, a frame includes 24 communication slots. Groups of 8 communication slots may be simultaneously transmitted using different frequencies. Communication slots may be assigned in any way. For example, a communication by a particular IoT device may be performed using a single assigned communication slot or, if necessary, multiple communication slots that may occur in parallel at different frequencies (channels) and/or subsequently. No communication slot may be assigned to multiple devices to prevent communication collisions. A frame (x04) ends with a beacon guard time (x14), during which no communications by any of the IoT devices that rely on the IoT communication protocol overlay may be allowed. However, other IoT devices that are merely capable of communicating using the underlying IoT communication protocol, but not the IoT communication protocol overlay, may communicate during the beacon guard time.

In total, the IoT communication protocol overlay (600) provides 72 communication slots (616). Accordingly, up to 72 individual communications may be performed in a single superframe (602). If these 72 communications are insufficient to serve all IoT devices, the protocol overlay may be modified in various ways without departing from the invention. For example, a superframe may be configured to include more than three frames. Additionally or alternatively, a frame may include more than three consecutive communication slots, and/or additional frequencies (channels) may be used to allow simultaneous transmission of additional communication slots. The same IoT communication protocol overlay may be used by all access points across a site.

In one or more embodiments of the invention, not all channels that are available in the underlying IoT communication protocol are used by the IoT communication protocol overlay. Channels that are not made available may be used to support devices that are not designed to work with the IoT communication protocol overlay, while being able to use the underlying IoT protocols. Such channels may also be used for lengthy transmissions such as a firmware provided over the air.

FIG. 7 shows a computing system in accordance with one or more embodiments of the invention. Embodiments of the invention may be implemented on a computing system. Any combination of mobile, desktop, server, embedded, or other types of hardware may be used. For example, as shown in FIG. 7, the computing system (700) may include one or more computer processor(s) (702), associated memory (704) (e.g., random access memory (RAM), cache memory, flash memory, etc.), one or more storage device(s) (706) (e.g., a hard disk, an optical drive such as a compact disk (CD) drive or digital versatile disk (DVD) drive, a flash memory stick, etc.), and numerous other elements and functionalities. The computer processor(s) (702) may be an integrated circuit for processing instructions. For example, the computer processor(s) may be one or more cores, or micro-cores of a processor. The computing system (700) may also include one or more input device(s) (710), such as a touchscreen, keyboard, mouse, microphone, touchpad, electronic pen, or any other type of input device. Further, the computing system (700) may include one or more output device(s) (708), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (700) may be connected to a network (712) (e.g., a local area network (LAN), a wide area network (WAN) such as the Internet, mobile network, or any other type of network) via a network interface connection (not shown). The input and output device(s) may be locally or remotely (e.g., via the network (712)) connected to the computer processor(s) (702), memory (704), and storage device(s) (706). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform embodiments of the invention.

Further, one or more elements of the aforementioned computing system (700) may be located at a remote location and connected to the other elements over a network (712). Further, embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

Figure 8:
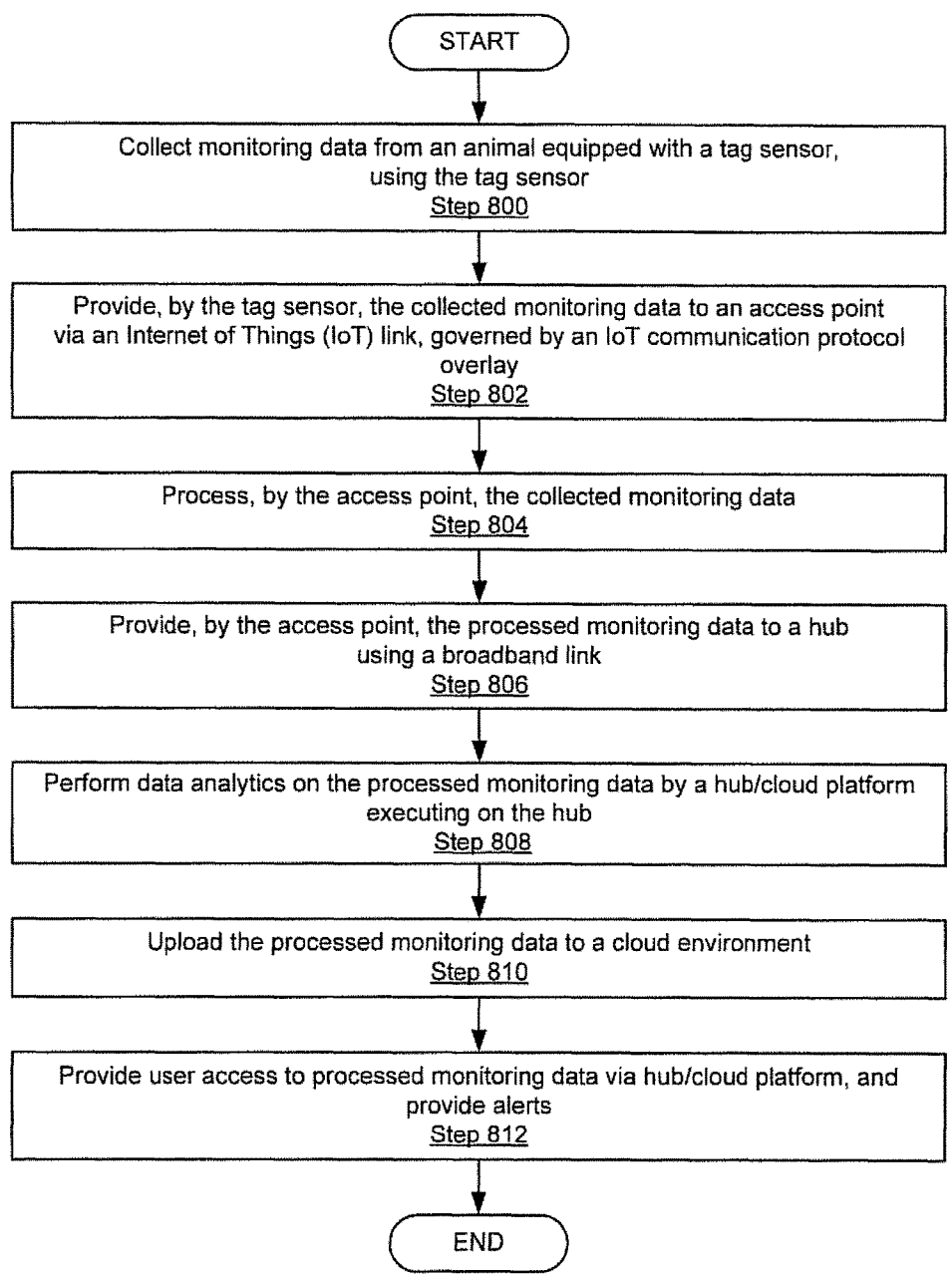
FIG. 8 shows a flowchart describing methods for monitoring livestock, in accordance with one or more embodiments of the invention.

FIG. 8 shows a flowchart describing methods for monitoring livestock, in accordance with one or more embodiments of the invention. The method may be used, for example, to track the location of livestock and/or physiological signals obtained from the animals. The method may be executed repeatedly over time, thus enabling a user to continuously monitor the animals and to detect changes, e.g., when the animals move.

In Step 800, monitoring data is collected from the animals that are equipped with tag sensors. Data may be collected from the various sensors of the tag sensor, but also from the in-vivo sensors, if in-vivo sensors are used. The collection may occur as scheduled, e.g., based on the time-base provided by the IoT communication protocol overlay or spontaneously, e.g., upon request or when a particular event is detected. The data collection by one tag sensor may be independent from the data collection by other tag sensors. The collected data may be buffered by the tag sensor until it can be transmitted to an access point.

In Step 802, the tag sensors provide the collected data to one or more access points, using the IoT link. Each tag sensor uses a communication slot at a particular time and in a particular frequency band, as specified by the IoT communication protocol overlay, thus avoiding transmission interference by multiple tag sensors using the same communication slot. The transmissions of the tag sensors may be received by one or more access points within range.

In Step 804, the received data may be processed by the access point(s) that received the data. The processing may include aggregating, filtering, fusing, compressing and/or encrypting the data. The processing may further include the exchange of data with other access points. For example, TDOA data may be exchanged between access points to determine a location of a tag sensor, relative to the access points.

In Step 806, the processed data are provided to a hub, using the broadband link that interfaces the access point(s) and the hub. Step 806 is optional and is executed only if a hub exists in the used system configuration. If no hub exists, the processed data may alternatively be provided to the cloud. Regardless of whether the system is configured to use a hub, a cloud or both, the processed data is received by the hub/cloud platform which is executing on the hub, in the cloud, or on the hub and in the cloud.

In Step 808, data analytics are performed by the hub/cloud platform executing on the hub. The data analytics may include modules that are generic to a variety of applications such as location tracking, and other modules that are specific to ranching, such as monitoring animals' physiological parameters. The data analytics may additionally or alternatively be performed in the cloud.

In Step 810, the processed monitoring data is uploaded to the cloud. This step may be performed in systems that include a cloud environment and in systems that include a combination of the hub and the cloud. Accordingly, data obtained from the tag sensors may be equally accessible via the cloud and via the hub.

In Step 812, a user is provided access to the processed monitoring data using the hub/cloud platform that is executing on the hub, in the cloud, or on the hub and in the cloud. The user may access the processed monitoring data using any type of computing device that is capable of interfacing with the hub/cloud platform. The user may obtain a visualization of the processed monitoring data, which may include text, graphics, charts, etc. The user may access a time history of the processed monitoring data and may further also access the unprocessed or partially processed data obtained from the tag sensors. Alerts may be provided to the user under certain configurable conditions. For example, an alert may be provided if an animal is leaving a particular area, if unusual movement patterns (such as no movement, indicating, for example, sickness, or excessive motion, indicating, for example, a predator) are detected, or if physiological measurements are beyond a specified range.

Various embodiments of the invention have one or more of the following advantages. Embodiments of the invention enable comprehensive monitoring of livestock. The monitoring may include monitoring of animal location, animal behavior and/or animal physiology. The coverage provided by the monitoring system, in accordance with one or more embodiments of the invention, is scalable, from, e.g., tens of acres to tens of thousands of acres. The number of animals being monitored by the system for monitoring livestock, in accordance with one or more embodiments of the invention, is scalable, e.g., from hundreds of animals to hundreds of thousands of animals. The majority of the system's components may be operated on battery and/or solar power, with no access to the power grid and under hostile conditions including, but not limited to broad temperature ranges, wind, rain, dust, insects and mechanical stress, in accordance with one or more embodiments of the invention. Systems for monitoring livestock, in accordance with one or more embodiments of the invention, may be operated in environments that offer hardwired, wireless or no broadband Internet access.

Embodiments of the invention may enable, for example, the implementation of geo-fencing functionalities to prevent escape or to detect proximity to hazardous features such as cliffs. Embodiments of the invention may further enable the detection of regular use (or failure to use) feed or water locations, rapid movements (resulting, e.g., from a predator attack), and/or failure to move (resulting, e.g., from injury). Further additional behaviors may be detected using additional sensors. For example, an accelerometer may be used to detect head motion that is characteristic for eating and drinking. Physiological variables may be monitored, including temperature, heart rate, blood pressure and digestive activity to monitor animal health. Alerts may be triggered when any one or combinations of measurements are beyond a specified range, thus enabling early detection of threats, diseases and other anomalies.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system for monitoring livestock in a ranching environment, the system comprising:
  a two-tier access point comprising a first tier broadband communication interface and a second tier narrowband communication interface, and configured to:
    receive, using the second tier narrowband communication interface and using an Internet of Things (IoT) protocol, monitoring data from tag sensors that are attached to animals and configured to collect the monitoring data from the animals; and
    transmit, using the first tier broadband communication interface, the received monitoring data to a hub/cloud platform that provides a user interface enabling a user to monitor the livestock,
    wherein the IoT protocol comprises a repeating pattern of superframes, each superframe comprising a plurality of frames, wherein the repeating pattern of superframes governs wireless data communication between the two-tier access point and the tag sensors.

2. The system of claim 1, wherein the second tier narrowband communication interface is an Internet of Things (IoT) interface.

3. The system of claim 2, wherein the IoT interface is based on one selected from a group consisting of a LoRa and a SigFox protocol.

4. The system of claim 1, wherein the first tier broadband communication interface is a wireless local area network (WLAN).

5. The system of claim 4, wherein the WLAN is based on the Wi-Fi standard.

6. The system of claim 1, further comprising additional two tier access points, wherein the access point and the additional two tier access points interface using the first tier broadband communication interface.

7. The system of claim 6, wherein the interfacing two tier access point and the additional two-tier access points form a mesh.

8. The system of claim 7, wherein the two tier access point is a primary access point, providing an uplink, and each of a subset of the additional two tier access points directly interfaces with the primary access point.

9. The system of claim 7, wherein the two tier access point is a primary access point, providing an uplink, and a subset of the additional two tier access points interface with the primary access point in a daisy-chain configuration.

10. The system of claim 6, wherein the two tier access point and the additional two tier access points provide a spatially overlapping coverage in a region, enabling a tag sensor to simultaneously communicate with at least three of the two tier access points.

11. The system of claim 6, further comprising a hub proving an uplink to a cloud environment, wherein the hub/cloud platform executes on at least one selected from a group consisting of the hub and the cloud environment.

12. The system of claim 1, wherein one of the tag sensors comprises:
  sensors configured to obtain measurements from the animal equipped with the tag sensor;
  a processor configured to process the obtained measurements;
  an IoT transceiver, configured to transmit the processed measurements to the first access point;
  a battery that powers the tag sensor; and
  a fastener configured to affix the tag sensor to the animal.

13. The system of claim 12, wherein the one of the tag sensors further comprises an RFID tag, programmed with an identifier of the animal that can be read out by an RFID reader in proximity of the animal.

14. The system of claim 12, wherein the tag sensors comprise at least one selected from a group consisting of an accelerometer, a temperature probe, a heart rate sensor and a blood pressure sensor.

* * * * *